(12) United States Patent
Rathmacher et al.

(10) Patent No.: US 12,383,515 B2
(45) Date of Patent: Aug. 12, 2025

(54) COMPOSITIONS AND METHODS OF USE OF γ-KETOALDEHYDE SCAVENGERS FOR TREATING, PREVENTING OR IMPROVING NONALCOHOLIC FATTY LIVER DISEASE (NAFLD), NASH, ALD OR CONDITIONS RELATED TO THE LIVER

(71) Applicant: MTI Biotech, Inc., Ames, IA (US)

(72) Inventors: John Rathmacher, Story City, IA (US); Naji Abumrad, Nashville, TN (US); Charles Flynn, Nashville, TN (US)

(73) Assignee: MTI Biotech, Inc., Ames, IA (US)

( * ) Notice: Subject to any disclaimer, the term of this patent is extended or adjusted under 35 U.S.C. 154(b) by 0 days.

(21) Appl. No.: 18/077,832

(22) Filed: Dec. 8, 2022

(65) Prior Publication Data

US 2023/0181494 A1    Jun. 15, 2023

Related U.S. Application Data

(63) Continuation of application No. 15/697,193, filed on Sep. 6, 2017, now abandoned.

(60) Provisional application No. 62/410,133, filed on Oct. 19, 2016, provisional application No. 62/383,895, filed on Sep. 6, 2016.

(51) Int. Cl.
| | |
|---|---|
| *A61K 31/137* | (2006.01) |
| *A23L 33/00* | (2016.01) |
| *A23L 33/10* | (2016.01) |
| *A61K 31/195* | (2006.01) |
| *A61K 31/197* | (2006.01) |
| *A61K 31/44* | (2006.01) |
| *A61P 1/16* | (2006.01) |

(52) U.S. Cl.
CPC ............ *A61K 31/137* (2013.01); *A23L 33/10* (2016.08); *A23L 33/30* (2016.08); *A23L 33/40* (2016.08); *A61K 31/195* (2013.01); *A61K 31/197* (2013.01); *A61K 31/44* (2013.01); *A61P 1/16* (2018.01); *A23V 2002/00* (2013.01)

(58) Field of Classification Search
CPC .. A61K 31/137; A61K 31/195; A61K 31/197; A61K 31/44; A23L 33/10; A23L 33/30; A23L 33/40; C07C 215/50; C07C 217/58; C07C 215/46; A61P 1/16
See application file for complete search history.

(56) References Cited

U.S. PATENT DOCUMENTS

| | | |
|---|---|---|
| 6,794,398 B1 | 9/2004 | Nakamuta et al. |
| 2011/0117194 A1 | 5/2011 | Kim et al. |
| 2012/0157501 A1 | 6/2012 | Roberts, II et al. |
| 2014/0256774 A1 | 9/2014 | Roberts et al. |
| 2015/0265584 A1 | 9/2015 | Oates et al. |
| 2019/0099387 A1 | 4/2019 | Rathmacher et al. |
| 2023/0330049 A1* | 10/2023 | Rathmacher ......... A61K 31/137 |

FOREIGN PATENT DOCUMENTS

| | | |
|---|---|---|
| CN | 1628650 | 6/2005 |
| WO | 0023063 | 4/2000 |
| WO | 2008070778 A2 | 6/2008 |
| WO | 2013010034 A2 | 1/2013 |
| WO | 2013168013 A2 | 11/2013 |
| WO | 2016077279 A1 | 5/2016 |
| WO | 2017033119 A1 | 3/2017 |
| WO | 2019050967 A1 | 3/2019 |

OTHER PUBLICATIONS

Szabo et al. Nature reviews Gastroenterology & Hepatology 2015, 12, 387-400.*
Zhu et al. World J Gastroenterol 2008, 14 (29), 4677-4683.*
Longato et al. UEG Week 2014 Poster Presentation, Oct. 20, 2014, in United European Gastroenterology Journal 2014, 2 (1S), p. A136, poster P0018.*
Washington et al. Human Pathology 2000, 31 (7), 822-828.*
Ribeiro et al. Annu Rev Pathol 2022, 17, 345-365.*
Guan et al. Acta Biochim Biophys Sin 2022, 54 (11), 1577-1586.*
Roychowdhury et al., "Formation of γ-ketoaldehyde-protein adducts during ethanol-induced liver injury in mice", Free Radical Biology and Medicine, Jul. 17, 2009, pp. 1526-1537, vol. 47.
"Definition of Prevent", WordNet Search—3.1 Glossary http://wordnetweb.princeton.edu/perl/webwn?c=0&sub=Change&o2=&o0=1&o8=1&ol= . . . Sep. 18, 2012.
Amarnath, Venkataraman , et al., "Pyridoxamine: An Extremely Potent Scavenger of 1,4-Dicarbonyls", Chem. Res. Toxicol, 17:3, 410-415.
Chalasani, Naga , et al., "The Diagnosis and Management of Nonalcoholic Fatty Liver Disease: Practice Guidance From the American Association for the Study of Liver Diseases", Hepatology, 67:1, 328-357.
Dancygier, Henryk , "Clinical Hepatology: Principles and Practice of Hepatobiliary Diseases", vol. 1-2.
Davies, Sean S., et al., "Reactive Carbonyl Species Scavengers—Novel Therapeutic Approaches for Chronic Diseases", Curr Pharmacol Rep., 3:2, 51-67.
Gaens, Katrien , et al., "Endogenous formation of N-(carboxymethyl)lysine is increased in fatty livers and induces inflammatory markers in an in nitro model of hepatic steatosis", Journal of Hepatology, vol. 56, 2012, 647-655.
Kanth, Vishnubhotla Venkata Ravi, et al., "Genetics of non-alcoholic fatty liver disease: From susceptibility and nutrient interactions to management", World Journal of Hepatology, 8:20, 827-837.
Longato , et al., "Activation of JNK Mudulates the Profibrogenic Action of Myostatin in Hepatic Stellate Cells (JSC)", Hepatology, vol. 60, No. 1, 2014, 579A.
Noureddin, Mazen , et al., "Promising therapies for treatment of nonalcoholic steatohepatitis", Expert Opinion on Emerging Drugs, 21:3, 347-357.

(Continued)

*Primary Examiner* — Irina Neagu
(74) *Attorney, Agent, or Firm* — Dentons Davis Brown; Emily E. Harris

(57) ABSTRACT

Methods and compositions for use in treating, preventing or improving diseases related to the liver in an animal, including but not limited to nonalcoholic fatty liver disease (NAFLD), alcoholic liver disease (ALD) or nonalcoholic steatohepatitis (NASH), are described. The compounds of the present invention are gamma-ketoaldehyde scavengers.

6 Claims, 20 Drawing Sheets

(56) References Cited

OTHER PUBLICATIONS

Wetzels, Suzan, et al., "Advanced Glycation Endproducts Are Increased in the Animal Model of Multiple Sclerosis but Cannot Be Reduced by Pyridoxamine Treatment or Glyoxalase 1 Overexpression", International Journal of Molecular Sciences, 19:5, 1-19.

Yokohama, Shiro, et al., "Therapeutic Efficacy of an Angiotensin II Receptor Antagonist in Patients with Nonalcoholic Steatohepatis", Concise Communication, 40:5, 1222-1225.

Zagol-Ikapitte, Irene, et al., "Determination of the Pharmacokinetics and Oral Bioavailability of Saliclyamine, a Potent γ-Ketoaldehyde Scavenger, by LC/MS/MS", pharmaceutics, vol. 2, Feb. 1, 2010, 18-29.

Guo, Lilu, et al., "Isolevuglandin-Type Lipid Aldehydes Induce the Inflammatory Response of Macrophages by Modifying Phophatidylethanolamines and Activating the Receptor for Advanced Glycation Endproducts", Antioxidants & Redox Signaling, vol. 22, No. 18, 2015.

Maessen, Dionne E., et al., "Delayed Intervention With Pyridoxamine Improves Metabolic Funtion and Prevents Adipose Tissue Inflammation and Insulin Resistance in High-Fat Diet-Induced Obese Mice", Diabetes, vol. 65, 2016.

\* cited by examiner

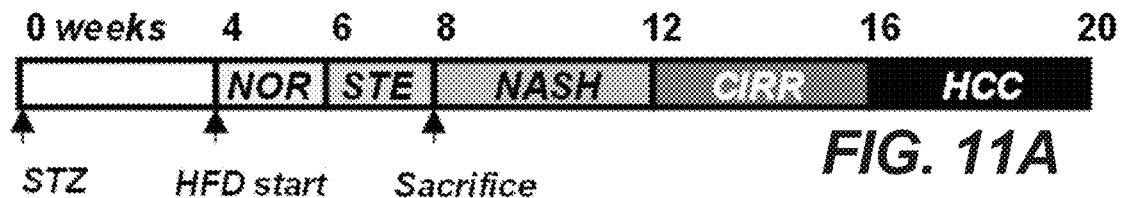
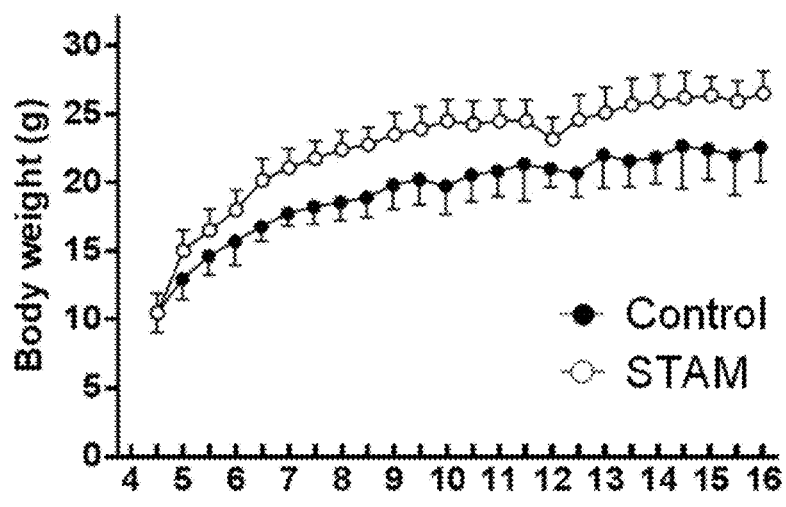
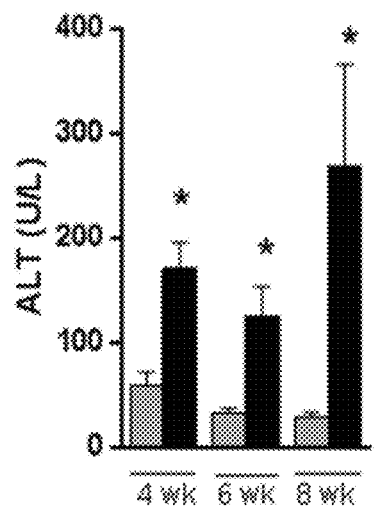
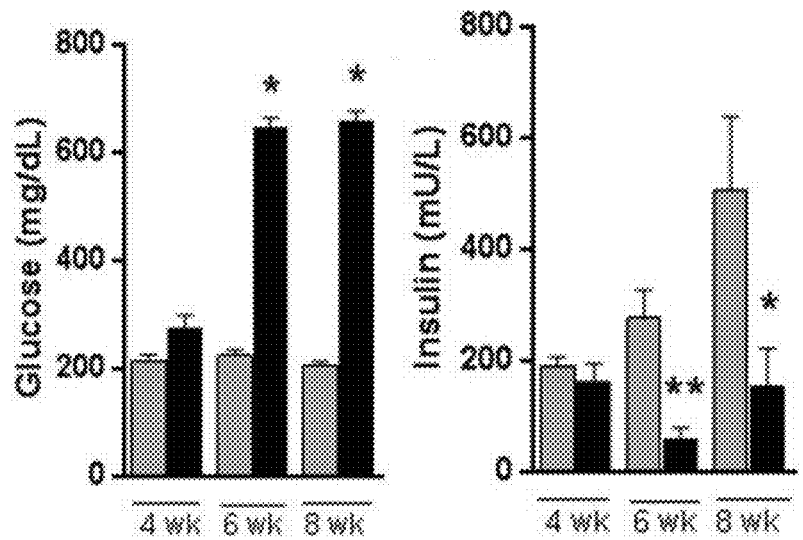
FIG. 11A, FIG. 11B, FIG. 11C, FIG. 11D, FIG. 11E

|  | 8 weeks | |
|---|---|---|
|  | Con | STAM |
| Steatosis | 0 | 3 |
| Ballooning | 0 | 1.75* |
| Inflammation | 0 | 0 |
| NAS Score | 0 | 4 * |
| Fibrosis Score | 0 | 0 |
*FIG. 11F*
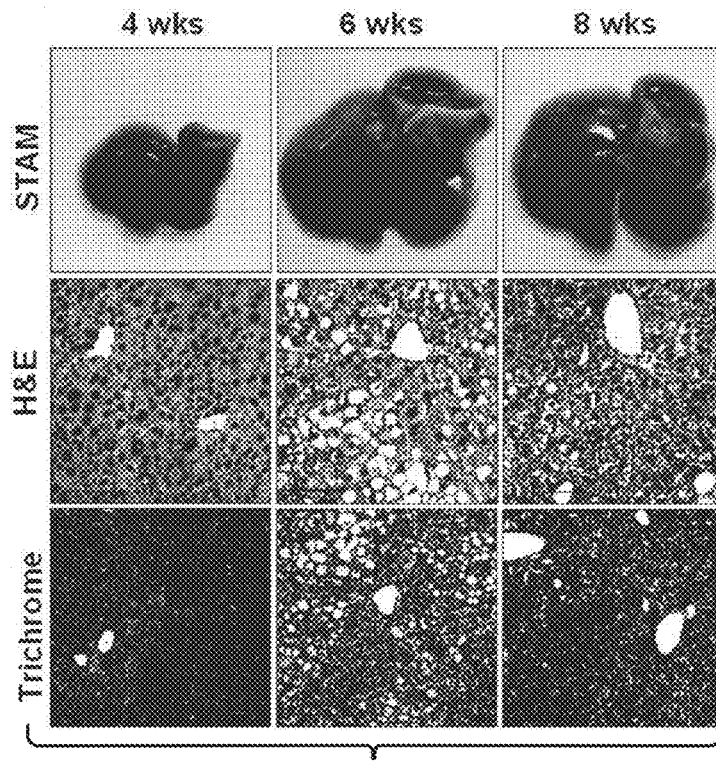
*FIG. 11G*
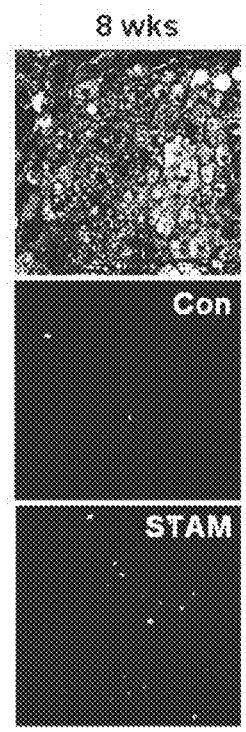
*FIG. 11H*
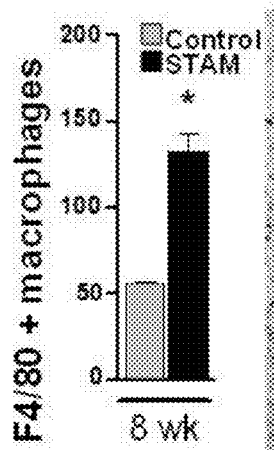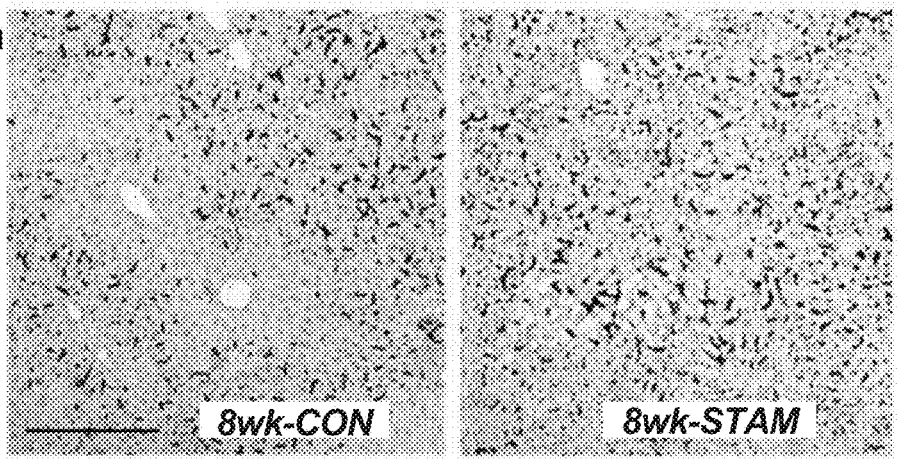
*FIG. 11I*

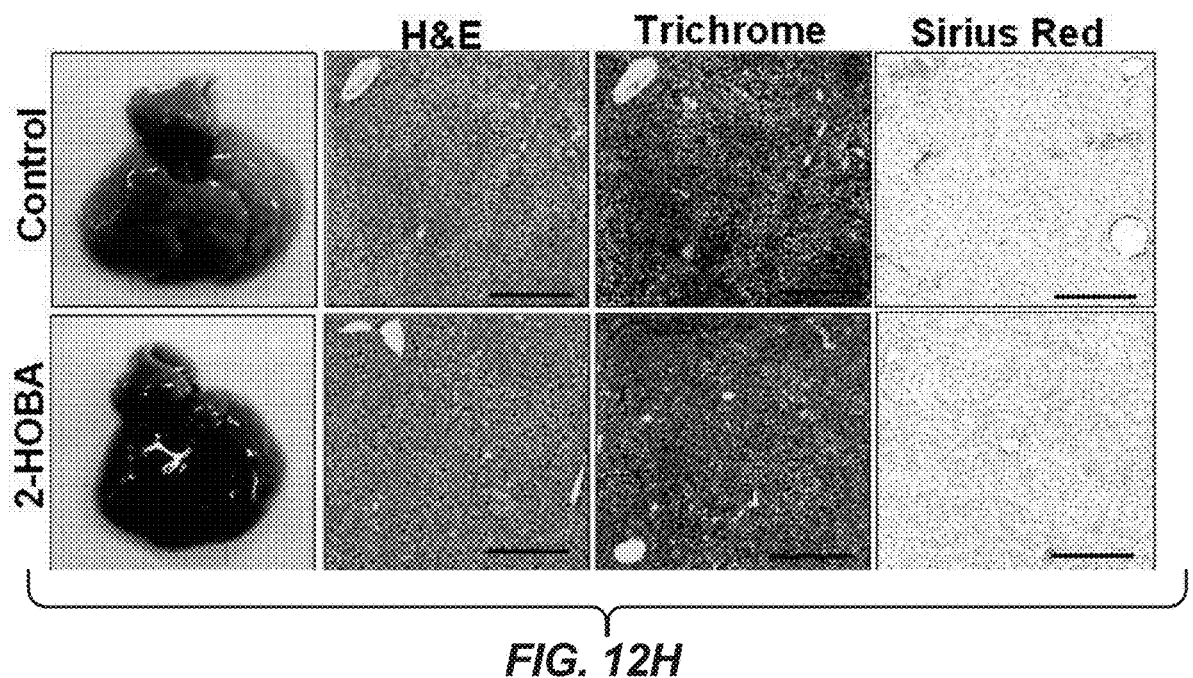
*FIG. 12H*
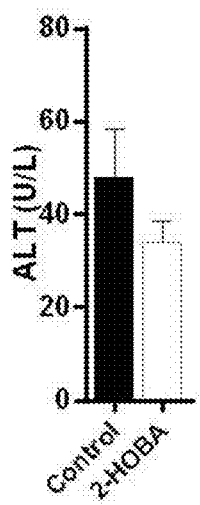 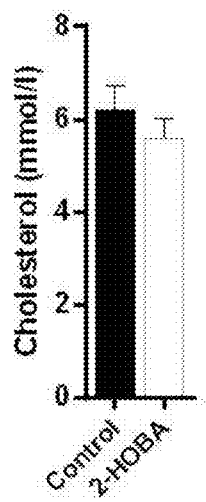 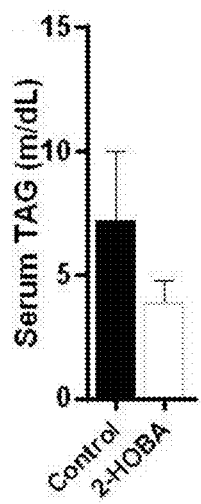
| | 8 weeks | |
|---|---|---|
| | Con | 2-HOBA |
| Steatosis | 1.2 | 0.7 |
| Ballooning | 1.8 | 2.0 |
| Inflammation | 1.1 | 0.3* |
| NAS Score | 4.2 | 3.0* |
| Fibrosis Score | 0 | 0 |
*FIG. 12I*   *FIG. 12J*   *FIG. 12K*   *FIG. 12L*

*gck*

*pck1*

*pdk4*

*irs1*

*irs2*

*pgc1α*

*cpt1a*

*gyk*

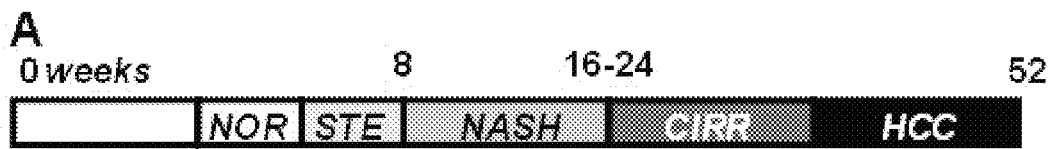
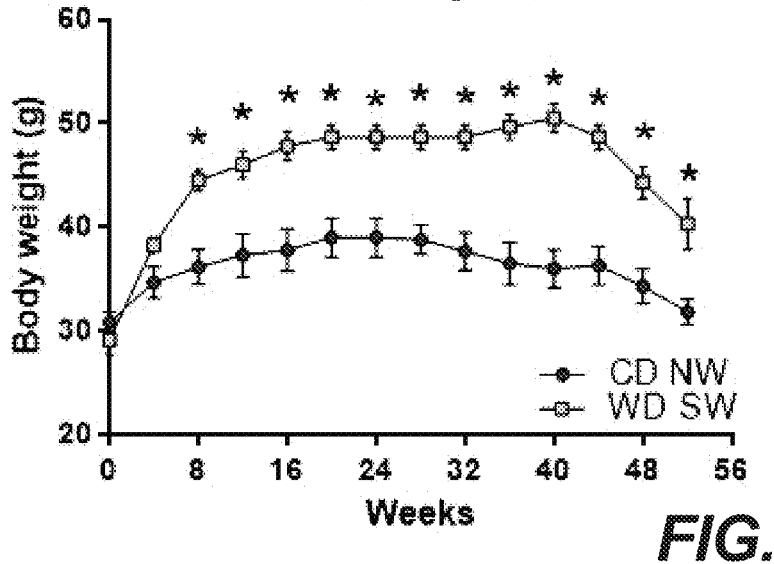
FIG. 14A
FIG. 14B
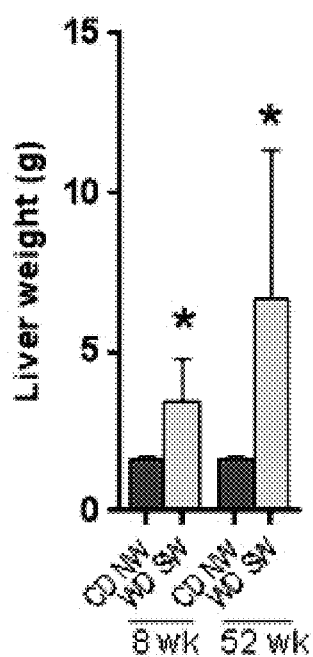 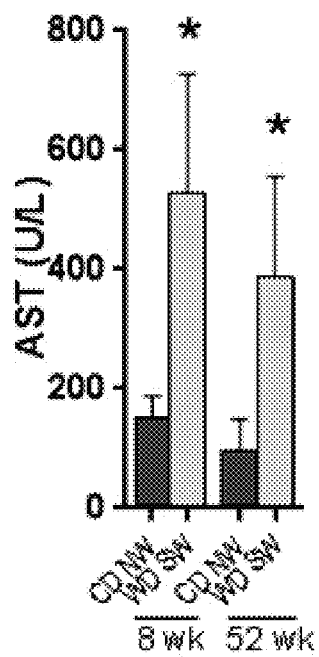 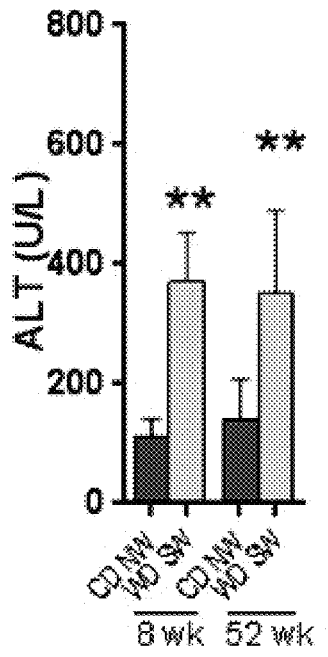
FIG. 14C   FIG. 14D   FIG. 14E

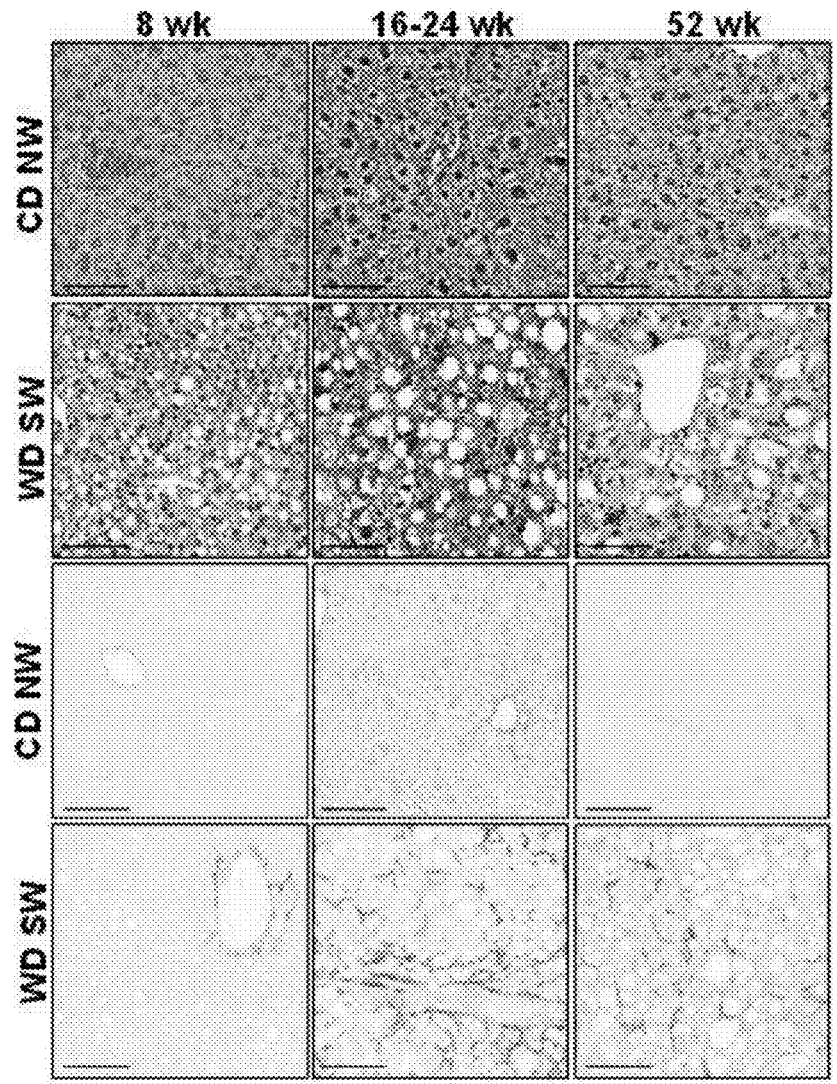
*FIG. 14F*
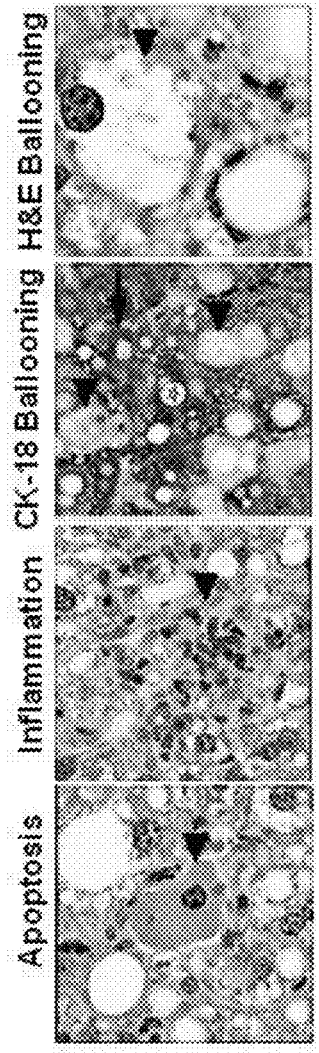
*FIG. 14H*
|  | 8 weeks | | 16-24 weeks | | 52 weeks | |
| --- | --- | --- | --- | --- | --- | --- |
|  | CD NW | WD SW | CD NW | WD SW | CD NW | WD SW |
| Steatosis | 0 | 3 | 0 | 3 | 0 | 2.5 |
| Ballooning | 0 | 1.75 | 0 | 0.5 | 0 | 1.3 |
| Inflammation | 0 | 0 | 0 | 0.5 | 0 | 1.75* |
| NAS Score | 0 | 4 | 0 | 4.5 | 0 | 5 |
| Fibrosis Score | 0 | 0 | 0 | 0.6 | 0 | 2.5* |
*FIG. 14G*

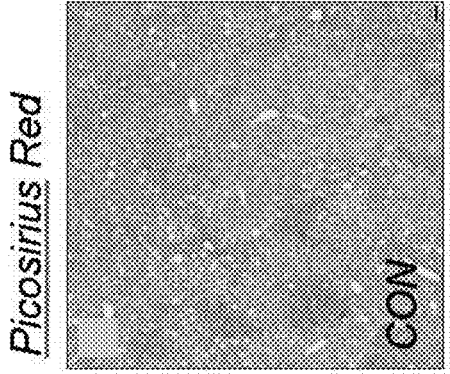
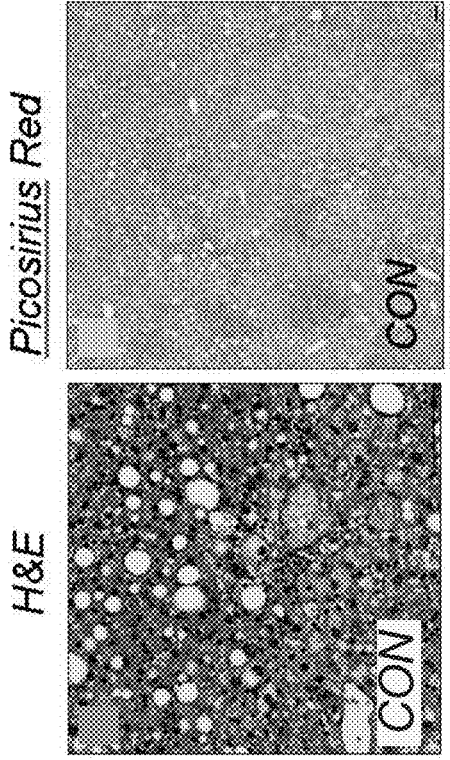
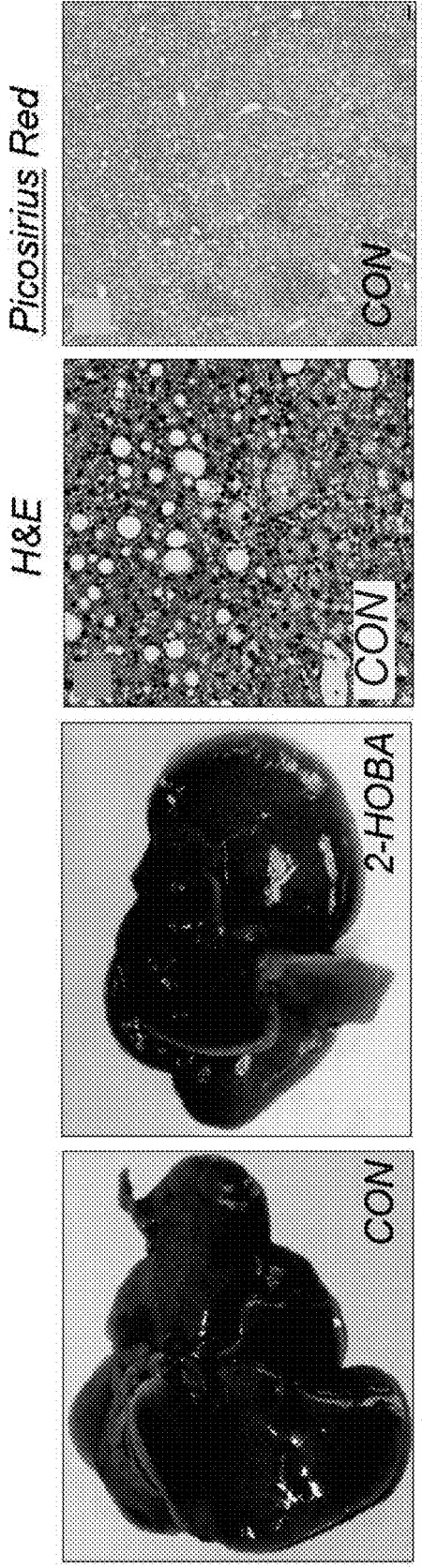
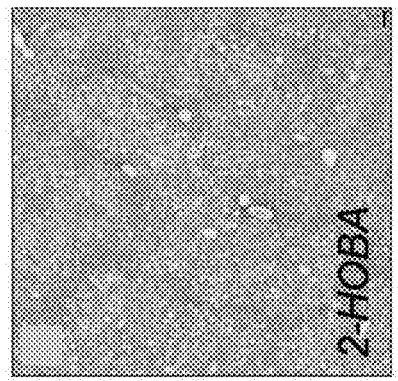
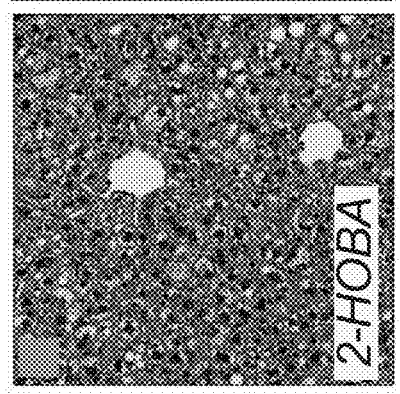
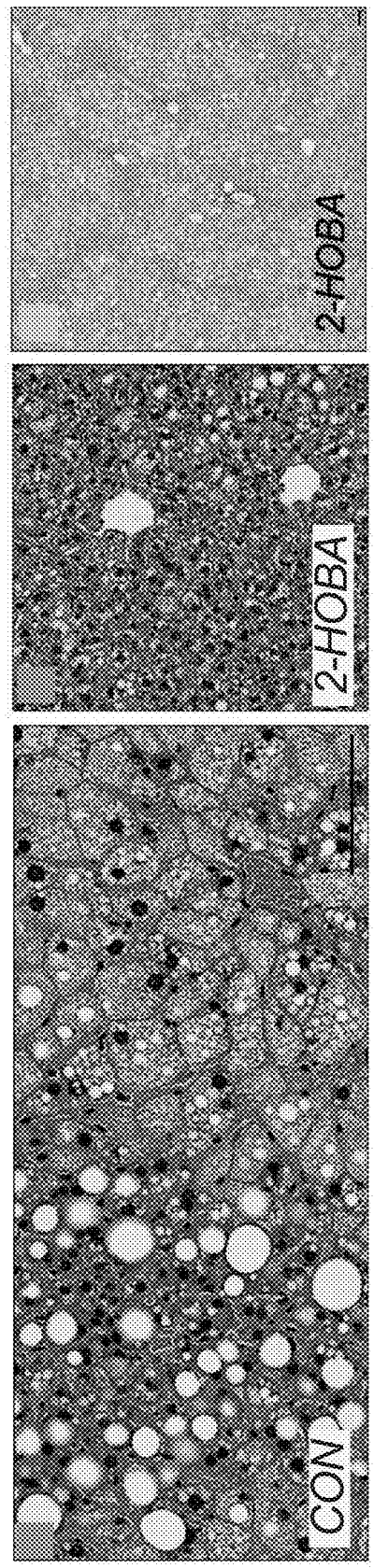

COMPOSITIONS AND METHODS OF USE OF γ-KETOALDEHYDE SCAVENGERS FOR TREATING, PREVENTING OR IMPROVING NONALCOHOLIC FATTY LIVER DISEASE (NAFLD), NASH, ALD OR CONDITIONS RELATED TO THE LIVER

This application is a Continuation of U.S. patent application Ser. No. 15/697,193, filed on Sep. 6, 2017, which claims priority from U.S. Provisional Patent Application 62/383,895, filed on Sep. 6, 2016, and from U.S. Provisional Patent Application 62/410,133, filed on Oct. 19, 2016, which are herein incorporated by reference in their entireties.

BACKGROUND OF THE INVENTION

1. Field

The present invention relates to a composition comprising a γ-ketoaldehyde (γ-KA) scavenging compound, such as 2-Hydroxybenzylamine (2-HOBA), and methods of administering a γ-KA scavenger to treat, prevent or improve diseases or conditions relating to the liver including nonalcoholic fatty liver disease (NAFLD) and/or alcoholic liver disease (ALD), and/or nonalcoholic steatohepatits (NASH).

2. Background

Chronic liver disease due to alcohol is a leading cause of morbidity and mortality that continues to rise. Second to viral hepatitis, chronic ethanol overconsumption is responsible for 25% of all deaths caused by liver cancer and cirrhosis. Chronic alcohol consumption is a frequent comorbidity of liver disease and cancer. The burden of health care for alcoholic liver disease (ALD) is high with cost estimates approaching $27 billion per year in the U.S. alone. Abstinence is the best therapy for ALD but recidivism is a major risk with relapse rates ranging from 67%-81% over the course of a year.

ALD includes a range of hepatic manifestations including fatty liver (steatosis), hepatitis and cirrhosis/fibrosis that may present simultaneously in a given individual. The spectrum of ALD ranges from simple steatosis to alcoholic steatohepatitis (ASH) to cirrhosis and is aggravated with obesity. There are many mechanisms by which alcohol induces liver injury; however, inflammation underpins the advancement of ALD. Ethanol metabolism promotes antioxidant depletion and leads to the formation of injurious entities including acetaldehyde, acetate, reactive oxygen species (ROS), and lipid peroxides that induce inflammatory responses. Additionally, alcohol and its metabolites incite inflammation by promoting gut leakiness and stimulating immune cells (the so-called adaptive immune response) and/or activating innate immune pathways, such as complement. While activation of innate immunity components initiates alcoholic liver injury it also triggers hepatoprotective, regenerative, and anti-inflammatory responses that reduce hepatocyte damage.

It is well known that lipid peroxidation and oxidative stress play significant roles in inflammation and the pathogenesis of chronic liver disease, especially ALD. Aldehydes such as malondialdehyde (MDA) and 4-hydroxynonenol (4-HNE) form covalent protein adducts which interfere with normal protein function. Orders of magnitude more reactive than MDA and 4-HNE are the peroxidation products of arachidonic acid, termed acyclic γ-KAs (also known as isolevuglandins or isoketals), which are key mediators of inflammation (FIG. 1). γ-KAs adduct rapidly and covalently to proteins and DNA, interfere with normal molecule function, and form protein-protein cross-links (isoketals). γ-KAs are produced by the F2-Isoprostane ($F_2$-IsoP) pathway. The γ-KAs have been shown to accumulate in various pathophysiological conditions through the non-classic eicosanoids, isoprostanes (IsoP) and isofurans (IsoF) that are formed non-enzymatically by free radical mediated peroxidation of arachidonic acid. Isofurans are similar to the isoprostanes, but contain a substituted tetrahydrofuran ring. It has been demonstrated that anti-γ-KA antibody titers in the serum of human subjects with ALD are elevated relative to subjects without ALD (FIG. 2).

ALD is characterized by the development of steatosis, inflammation, hepatocyte necrosis and apoptosis, with the eventual development of fibrosis and cirrhosis. It is also well established that consumption of alcohol in excess causes an oxidative injury to the liver. $F_2$-IsoPs have been shown to be the most accurate predictors of oxidative stress in vivo, and their levels are increased in alcoholic liver disease, and chronic hepatitis. Over-production of KAs is implicated in the pathogenesis of several chronic inflammatory diseases. More recently, ethanol feeding in the mouse has been shown to induce formation of hepatic γ-KAs which readily bind to proteins to form stable adducts. These γ-KA-protein adducts are likely to contribute to ethanol-induced liver injury by eliciting proinflammatory responses or adduct-specific immune responses.

There is considerable interest in identifying appropriate therapeutic interventions aimed at inhibiting the inflammatory processes and interrupting the immunogenic pathways associated with ALD. 2-hydroxy-benzylamine (2-HOBA), a staple of buckwheat, was found to be a potent scavenger of γ-KAs scavenging γ-KAs 980-fold faster than the rate of formation of γ-KA-lysyl-protein adducts. Importantly, they showed that this γ-KA scavenger does not inhibit cyclooxygenase enzymes. In a model of oxidant mediated cell death (FIG. 3), 2-HOBA almost completely prevented cell death induced by t-butylhydroperoxide (tBHP). In addition, it was demonstrated that 2-HOBA has a protective effect against oxidant mediated cell death HepG2 cells exposed to varying concentrations of hydrogen peroxide ($H_2O_2$).

Despite the profound economic and health impacts of ALD, little progress has been made in the management of patients with this severe clinical condition. While abstinence is a cornerstone of treatment, there is considerable interest in identifying other therapeutic interventions and treatments for ALD. Current therapeutic modalities for ALD include corticosteroids and pentoxyfilline. Corticosteroids improve short-term survival of severe forms of alcoholic hepatitis, but are frequently contraindicated. Pentoxyfilline, a competitive non-selective phosphodiesterase inhibitor, improved short-term survival in severe acute alcoholic hepatitis and demonstrated improved risk-benefit profiles compared to prednisone, but when combined with prednisone it did not confer additional benefit. Both of these treatments attenuate the inflammatory response but do not target the underlying inflammatory signal(s). The trapping of toxic oxidized lipids by 2-HOBA is novel in that it attenuates the formation of aggravating protein adducts that sustain inflammation and drive liver injury. The present invention includes use of 2-HOBA for preventing ALD and also attenuating the propagation of alcoholic liver disease.

Epidemiological data indicate that nonalcoholic fatty liver disease (NAFLD) is the most prevalent form of chronic liver disease in western countries. The spectrum of NAFLD ranges from simple steatosis to nonalcoholic steatohepatits (NASH) to cirrhosis and occurs frequently in the setting of obesity, dyslipidemia and insulin resistance. NASH can lead to cirrhosis and liver failure in 10-15% of patients. The mechanisms discriminating steatosis from NASH are still not entirely understood. It is increasingly evident that inflammation and the consequent production of reactive oxygen species (ROS) and reactive lipid species (RLS) are important components in the pathogenesis of NASH. In the liver, the changes in the inflammatory and immune responses exacerbate ROS and pro-inflammatory cytokine production leading to worsening of NASH.

Further, patients with NAFLD and NASH have higher mortality and morbidity in comparison to the general population; NAFLD has increased cardiovascular mortality, NASH has more liver-related mortality. Recent observations concluded that NASH, currently the third most common indication for liver transplantation in the United States, is projected to become the most common indication for liver transplantation in the next 10 years. NASH is the inflammatory form of NAFLD and is characterized by excess liver fat, inflammation, and hepatocellular ballooning with or without fibrosis. NASH is most concerning for progression to end stage liver disease, or cirrhosis. The mechanisms and conditions favoring NASH are unclear but histologically, it bears resemblance to alcoholic steatohepatitis. It is well-known that lipid peroxidation and oxidative stress play significant roles in the pathogenesis of chronic liver disease including NASH. Reactive oxygen species (ROS) accelerate the formation of lipid peroxides, leading to generation of bifunctional electrophiles (BFEs) that are key mediators of inflammation. Among these BFEs, 4-hydroxynonenal (4-HNE), acrolein, malondialdehyde (MDA), methylglyoxal (MGO) and levuglandins (LGs) are known to mediate oxidative injury by covalently modifying lipids, proteins and DNA. BFEs are extremely reactive compounds that adduct covalently to proteins and DNA, interfere with normal molecule function, and form protein-, phosphoethanolamine- and DNA-cross-links.

Nonalcoholic steatohepatitis (NASH) is liver inflammation and damage caused by a buildup of fat in the liver. NASH resembles ALD but occurs in people who consume little or no alcohol. NASH affects two to five percent of Americans, most often in people who are middle-aged and overweight or obese. The present invention includes use of 2-HOBA for preventing and/or treating NASH.

The present invention includes use of 2-HOBA to scavenge toxic oxidized lipids (ketoaldehydes) to effectively regulate the inflammatory program and lead to reversal in the associated hepatic injury.

The present invention includes use of 2-HOBA to target γ-KA to prevent lipid peroxidation and the resulting γ-KA-specific immune responses in alcoholic liver disease.

BRIEF DESCRIPTION OF THE FIGURES

FIG. 11A depicts the progression of NAFLD in the STAM model. FIG. 11B shows body weight over time in normal and streptozotocin-injected mice fed high fat diet for 16 weeks. FIG. 11C shows ALT elevation in control and STAM mice. FIG. 11D shows glucose elevation in control and STAM mice. FIG. 11E shows insulin reduction in control and STAM mice. FIG. 11F shows a table of individual NAS components and NAFLD activity scores in control and STAM mice. FIG. 11G shows representative livers and liver sections stained with H&E or Trichrome blue. FIG. 11H shows hepatocyte ballooning, inflammation and TUNEL-positive apoptotic bodies. FIG. 11I shows f4/80 positive macrophage content in control compared to STAM mice.

FIG. 12A shows body weight change over time in STAM mice. FIG. 12B shows liver weight. FIG. 12C shows liver-to-body-weight ratio. FIG. 12D shows hepatic 2-HOBA content. FIG. 12E shows plasma glucose comparisons. FIG. 12F shows insulin comparisons; FIG. 12G shows serum IsoProstanes comparisons. FIG. 12H demonstrates representative livers and liver sections stained with H&E, trichrome blue and Picosirius Red.

FIG. 12I shows serum ALT, FIG. 12J shows cholesterol and FIG. 12K shows tricglycerides.

FIGS. 12M-12T show gRT-PCR measurements of key genes in hepatic nutrient handling.

FIG. 13A shows pathways in insulin signaling. FIG. 13B shows immunoblots of total liver protein from control and 2-HOBA treated STAM mice. FIG. 13C shows pAKT Ser473/total AKT ratio. FIG. 13D shows pGSK3β Ser9/total pGSK3β ratio. FIG. 13E shows pmTOR pSer 2448/total mTOR ratio. FIG. 13F shows pThr202/Tyr204 pERK/total ERK ratio.

FIG. 14A-H depicts the development of NAFLD in DIAMOND™ mice. Specifically, 14A shows the progression of NAFLD in the DIAMOND model where B6/129 mice were fed a chow diet (CD) with normal water (NW) or high fat Western Diet (WD) with high fructose/glucose (SW) for up to 52 weeks. FIG. 14B shows body weight change over time, FIG. 14C shows liver weight; 14D AST, 14E ALT levels. FIG. 14F shows representative liver sections stained with H&E (top 2 rows) or Picosirius Red (bottom 2 rows. FIG. 14G shows hepatocyte ballooning, CK-18 stained ballooning, inflammation and apoptotic bodies.

FIG. 14H shows a table of components and NAFLD Activity Score FIG. 15A-K summarizes results of DIAMOND™ mice testing. FIGS. 14A-B are photos of DIAMOND mice at 28 weeks of age. FIG. 14C is a photo of a DIAMOND mouse after consuming 2-HOBA for 20 weeks. FIG. 14D shows an MRI if a mouse after 8 weeks of western diet feeding and 14E shows an MRI of a mouse after 8 weeks of western diet feeding and 2-HOBA consumption. FIG. 14F shows average weekly food intake and FIG. 14G shows average weekly body weight of DIAMOND mice with and without 2-HOBA supplementation. FIG. 14H shows mean liver/body weight ratio, FIG. 14I shows liver weight, FIG. 14J shows kidney weight and FIG. 14K shows pancreas weight of DIAMOND mice fed Western Diet (controls) or Western Diet with 2-HOBA (1 g/L) in drinking water for 20 wks.

FIG. 16A shows DIAMOND mouse liver at 28 wks of age after high fructose/glucose, high fat Western Diet feeding for 20 wks (control) or FIG. 16B with 2-HOBA (1 g/L) in drinking water for 20 wks. H&E stained micrographs of livers from FIG. C-FIG. D control DIAMOND mice or FIG. 16E those supplemented with 2-HOBA (1 g/L) in drinking water for 20 wks. Picosirius Red staining of FIG. 16F control and FIG. 16G 2-HOBA treated DIAMOND mouse livers. Serum ALT (FIG. 16H) and AST (FIG. 16I) of DIAMOND mice without and with 2-HOBA (1 g/L in drinking water) for 20 weeks. Liver steatosis (FIG. 16J), ballooning (FIG. 16K), inflammation (FIG. 16L), and composite NAFLD activity score (FIG. 16M) and fibrosis score (FIG. 16N) in control and 2-HOBA treated DIAMOND mice.

DETAILED DESCRIPTION OF THE INVENTION

Figure 1:
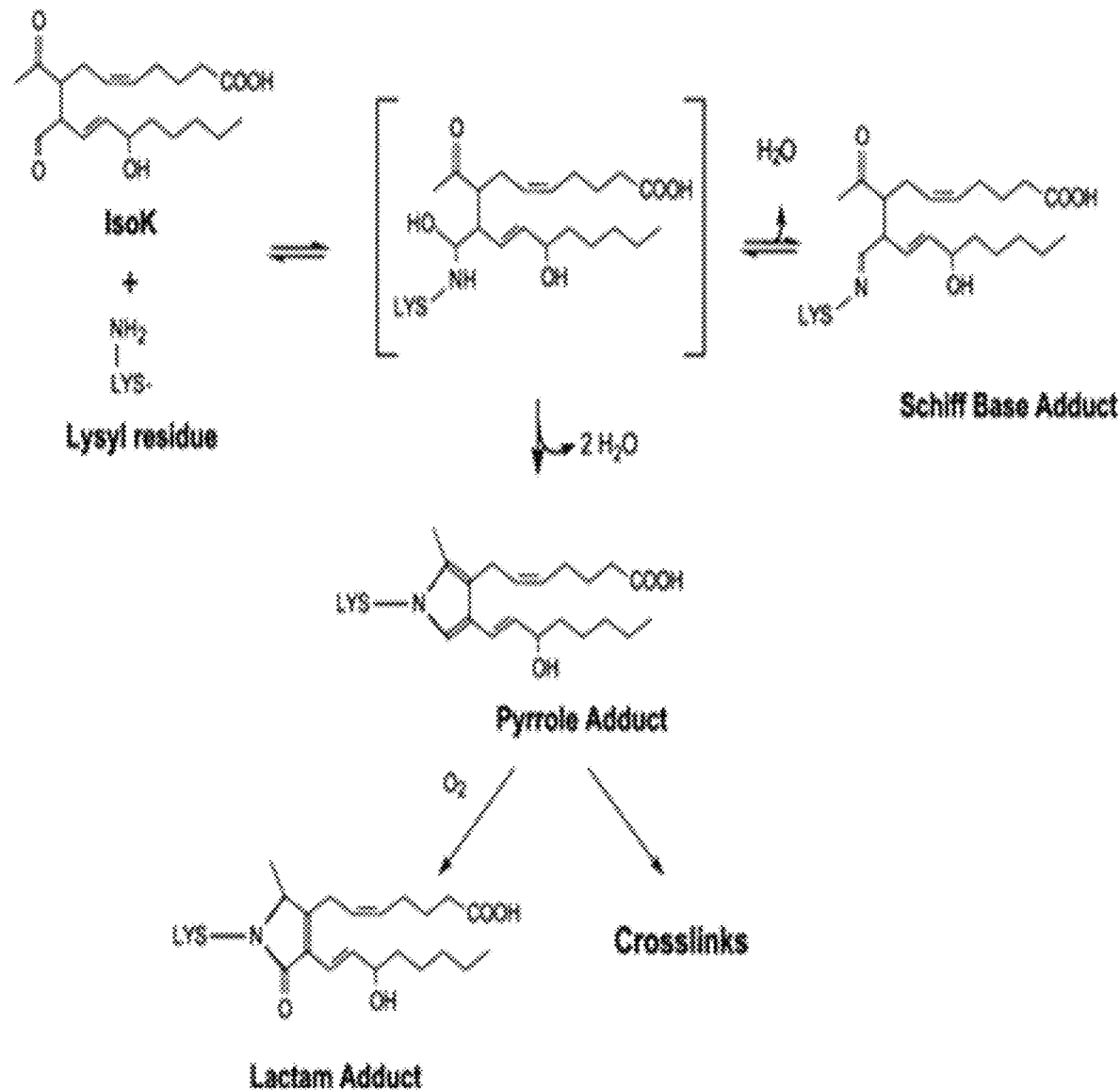
FIG. 1 is a graphic depicting how γ-KAs react with lysine or other primary amines to form a reversible Schiff base adducts.
Figure 2:
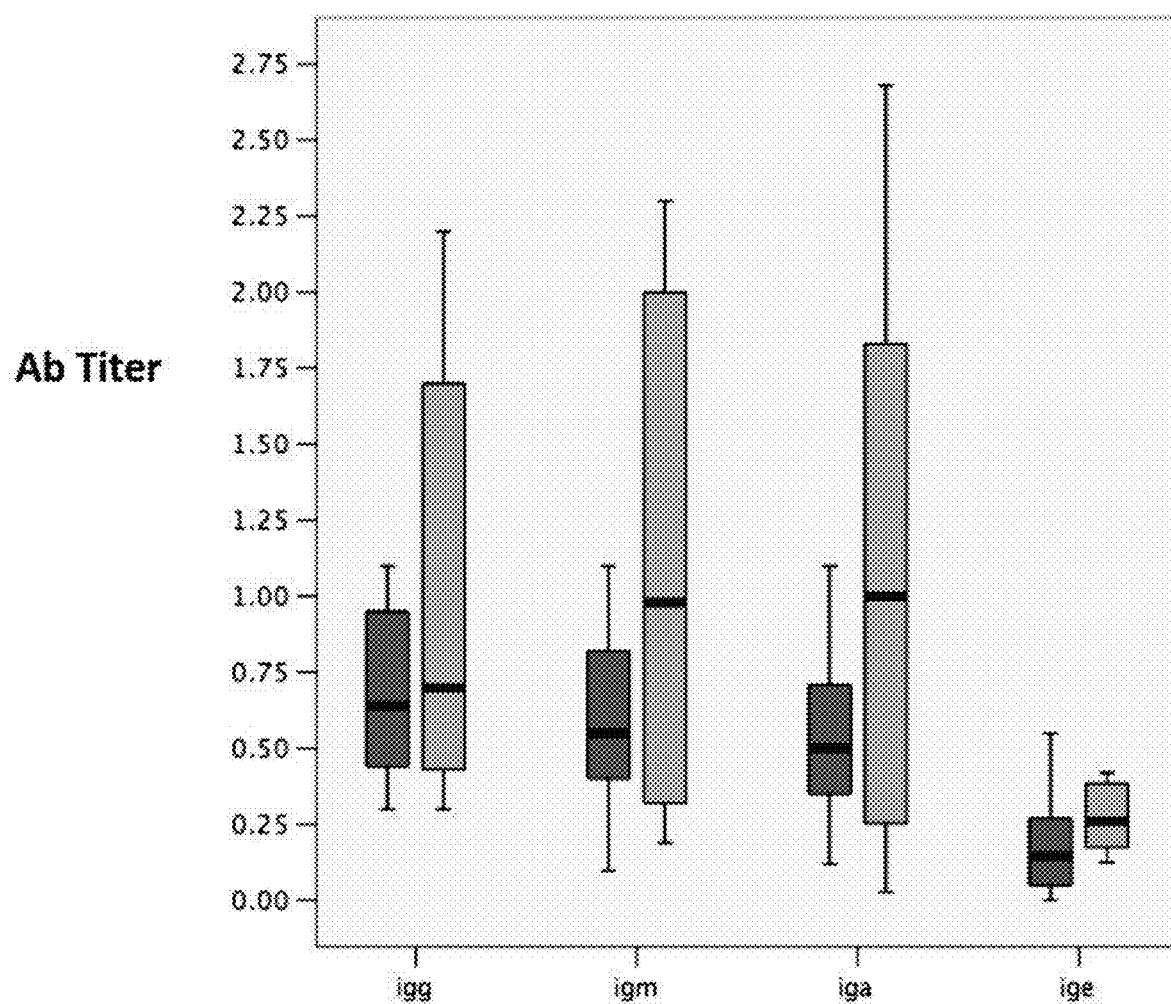
FIG. 2 is a graph depicting serum γ-KA antibody titers in hospitalized ICU patients with and without alcoholic liver disease.
Figure 3:
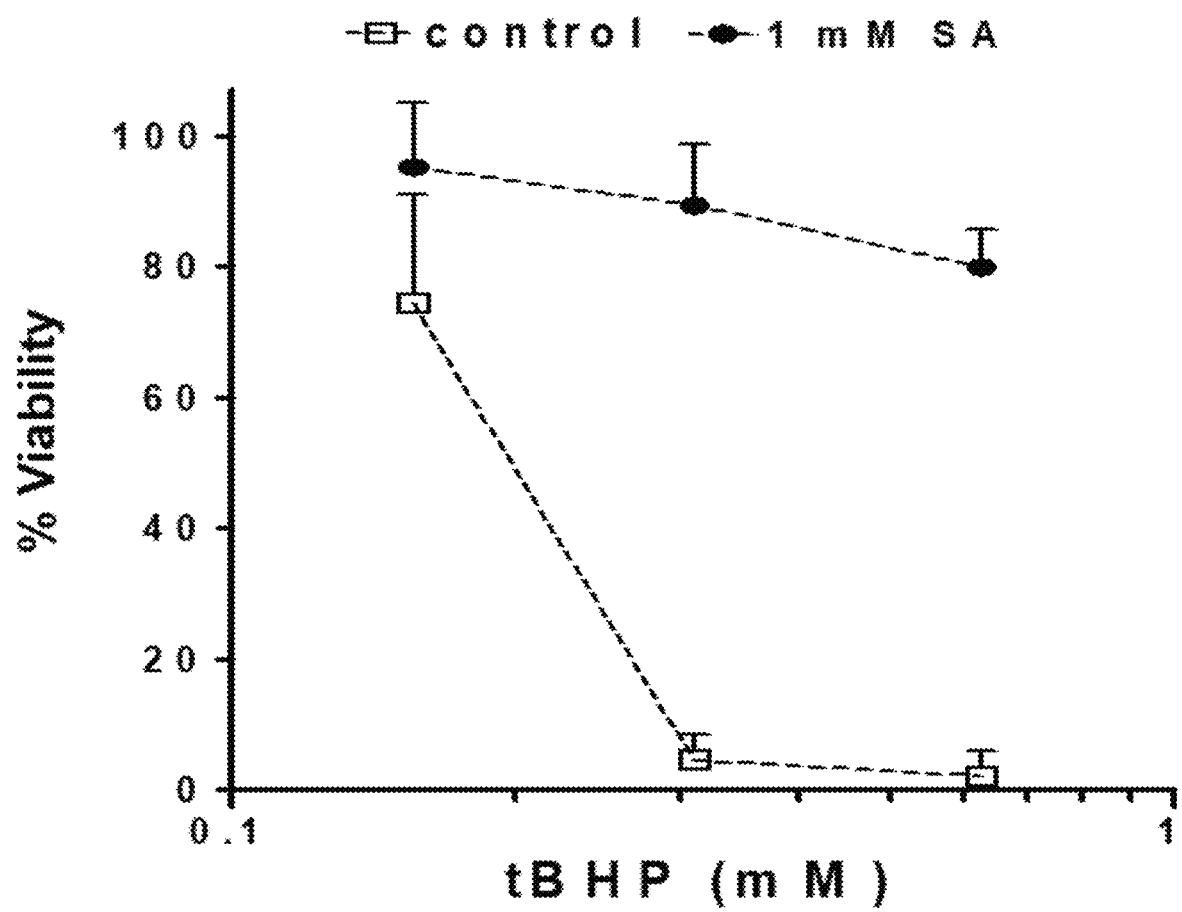
FIG. 3 is a graph depicting the protective effect of 2-HOBA against oxidant mediated cell death in mouse hepatocytes increasing t-butylhydroperoxide.

The present invention includes a novel nutritional therapy that will reduce liver injury by preventing the formation of γ-KA-protein adducts and differential effects on innate and adaptive immune responses. This nutritional therapy can be used to treat, prevent or improve conditions or diseases relating to the liver including but not limited to NAFLD, ALD and NASH. The nutritional therapy can be used to improve overall liver health and support healthy liver function.

The present invention comprises a means to specifically prevent the formation of γ-KA—adducts in the liver using a class of bifunctional electrophile (BFE) "scavenger" molecules. A series of phenolic amines that includes pyridoxamine and its water soluble derivative 2-hydroxybenzylamine (2-HOBA), a natural product of buckwheat seed comprise the preferred embodiment. 2-HOBA in particular reacts 980-fold faster with γ-KAs than with lysine, preventing protein and lipid adduction in vitro and in vivo.

The compositions and methods of this invention are directed to animals, including human and non-human animals. The animal may be healthy or may be suffering from a disease or condition.

The term administering or administration includes providing a composition to a mammal, consuming the composition and combinations thereof.

The present invention includes compositions and methods of use of 2-1HOBA, alternatively named salicylamine, SAM, 2-hydroxybenzylamine, and pentylpyridoxamine (PPM).

Embodiments of the present invention include compounds of the following formula, and their use as agents in a method for treating, preventing, or ameliorating liver conditions or diseases including NAFLD, ALD and NASH to a subject with or at risk of liver conditions or diseases including NAFLD, ALD and NASH, thereby inhibiting or treating the liver conditions or diseases:

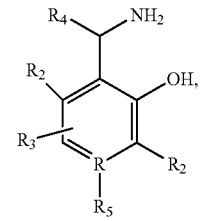

wherein:
R is N or C;
$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_3$ to form an optionally substituted $C_{3-8}$ membered ring containing C, O, S or N;
$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;
$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N;
$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N;
and stereoisomers and analogs thereof.

Another embodiment of the present invention includes compounds of the following formula, and their use in methods for treating, preventing, or ameliorating liver conditions or diseases including NAFLD, ALD and NASH to a subject with or at risk of these liver conditions:

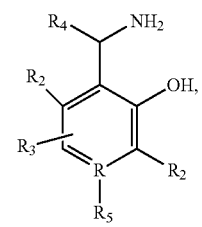

wherein:

R is N or C;

$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_4$ to form an optionally substituted $C_{3-8}$ membered ring containing C, O, S or N;

$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;

$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N;

$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N; and stereoisomers and analogs thereof.

In certain embodiments, the compound may be selected from the compounds disclosed herein. In a preferred embodiment, the compound may be salicylamine.

Another embodiment of the present invention is a method for treating, preventing, or ameliorating liver conditions or diseases including NAFLD, ALD and NASH to a subject with or at risk of liver conditions or diseases including NAFLD, ALD and NASH, thereby inhibiting or treating the liver conditions, comprising the step of co-administering to the subject at least one compound in a dosage and amount effective to treat the dysfunction in the mammal, the compound having a structure represented by a compound of the following formula:

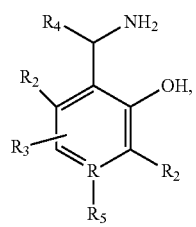

wherein:

R is N or C;

$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_4$ to form an optionally substituted $C_{3-8}$ membered ring containing C, O, S or N;

$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;

$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N;

$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N; and stereoisomers and analogs thereof; with a drug having a known side effect of treating, preventing, or ameliorating liver conditions or diseases including NAFLD, ALD and NASH.

Examples of compounds that may be used with the methods disclosed herein include, but are not limited to, compounds selected from the formula:

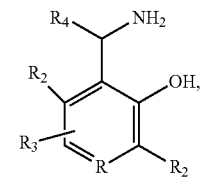

wherein:

R is N or C;

$R_2$ is independently H, substituted or unsubstituted alkyl;

$R_3$ is H, halogen, alkoxy, hydroxyl, nitro;

$R_4$ is H, substituted or unsubstituted alkyl, carboxyl; and pharmaceutically acceptable salts thereof.

In a preferred embodiment, the compound is salicylamine (2-hydroxybenzylamine or 2-HOBA).

The compound may be chosen from:

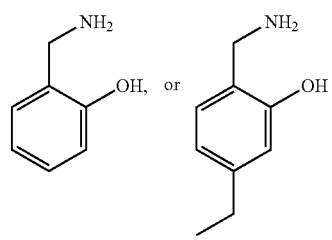

or a pharmaceutically acceptable salt thereof.

The compound may also be chosen from:

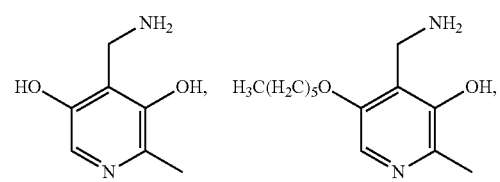

-continued

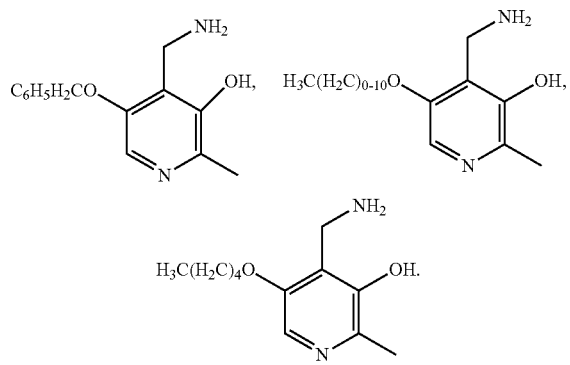

or a pharmaceutically acceptable salt thereof.

The compounds or analogs may also be chosen from:

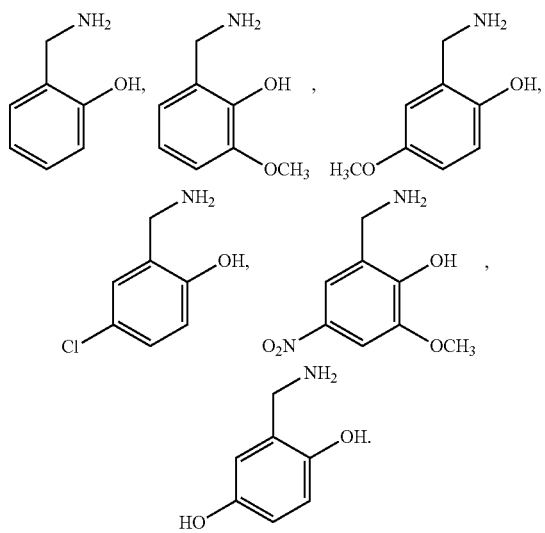

or a pharmaceutically acceptable salt thereof.

The compounds may also be chosen from:

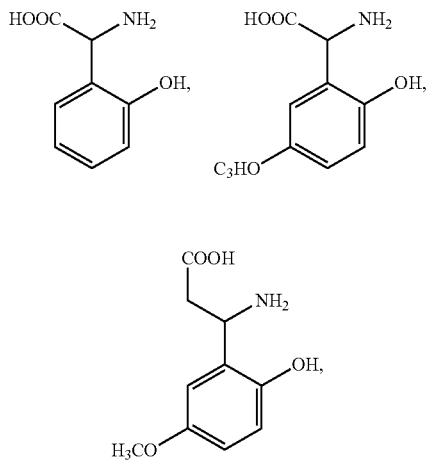

or a pharmaceutically acceptable salt thereof.

The compounds may also be chosen from

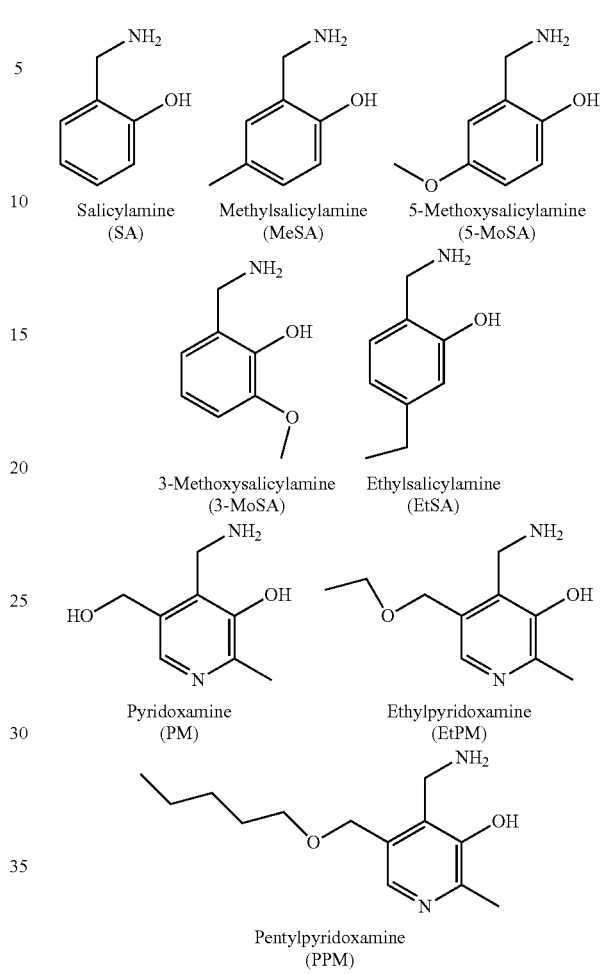

or a pharmaceutically acceptable salt thereof.

The compounds of the present invention can be administered by any method and such methods are well known to those skilled in the art and include, but are not limited to oral administration, transdermal administration, administration by inhalation, nasal administration, topical administration, intravaginal administration, ophthalmic administration, intraaural administration, intracerebral administration, rectal administration, and parenteral administration, including injectable administration such as intravenous administration, intra-arterial administration, intramuscular administration and subcutaneous administration. The compounds can be administered therapeutically, to treat an existing disease or condition, or prophylactically for the prevention of a disease or condition.

Although any suitable pharmaceutical medium comprising the composition can be utilized within the context of the present invention, preferably, the composition is combined with a suitable pharmaceutical carrier, such as dextrose or sucrose.

Methods of calculating the frequency by which the composition is administered are well-known in the art and any suitable frequency of administration can be used within the context of the present invention (e.g., one 6 g dose per day or two 3 g doses per day) and over any suitable time period (e.g., a single dose can be administered over a five minute time period or over a one hour time period, or, alternatively, multiple doses can be administered over an extended time period). The composition of the present invention can be administered over an extended period of time, such as weeks, months or years. The composition can be administered in individual servings comprising one or more than one doses (individual servings) per day, to make a daily serving comprising the total amount of the composition administered in a day or 24 hour period.

Any suitable dose of the present composition can be used within the context of the present invention. Methods of calculating proper doses are well known in the art.

"Treatment" or "treating" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

EXPERIMENTAL EXAMPLES

Example 1

Figure 4A:
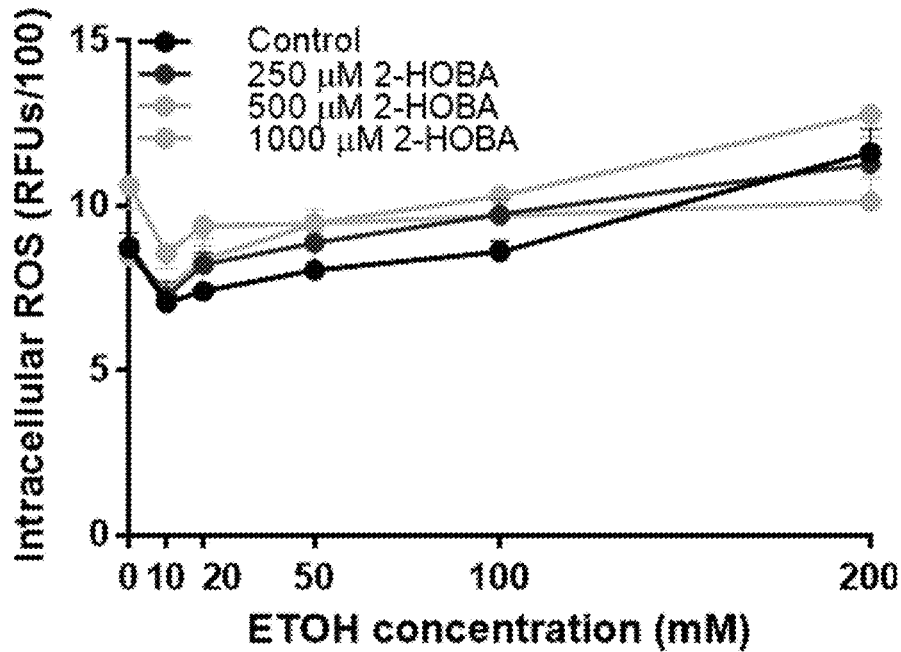
FIG. 4A depicts ROS is HepaRG with increasing ethanol dose and FIG. 4B depicts the protective effect of 2-HOBA with increasing ethanol concentration.
Figure 4B:
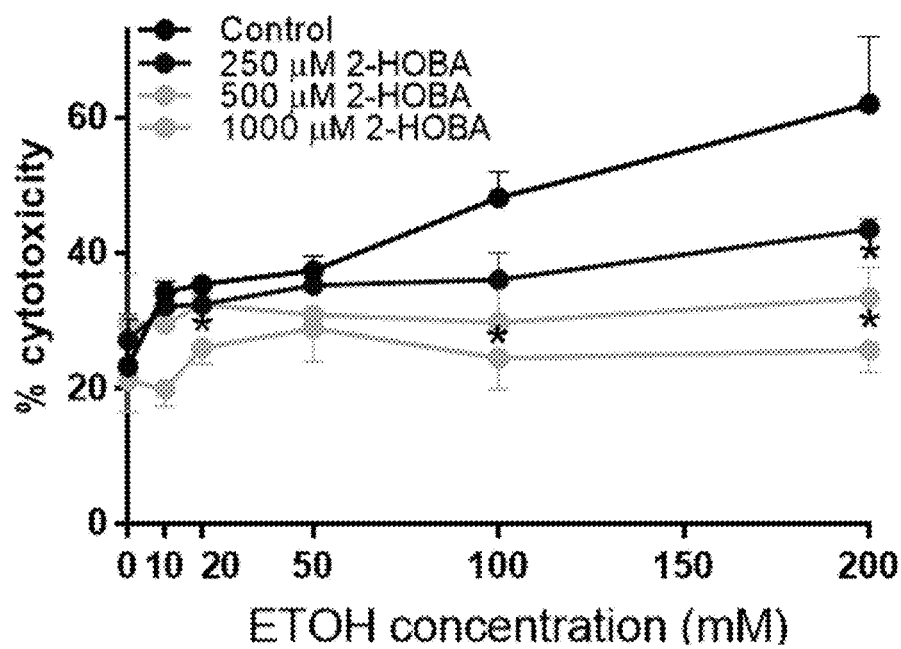
Figure 5A:
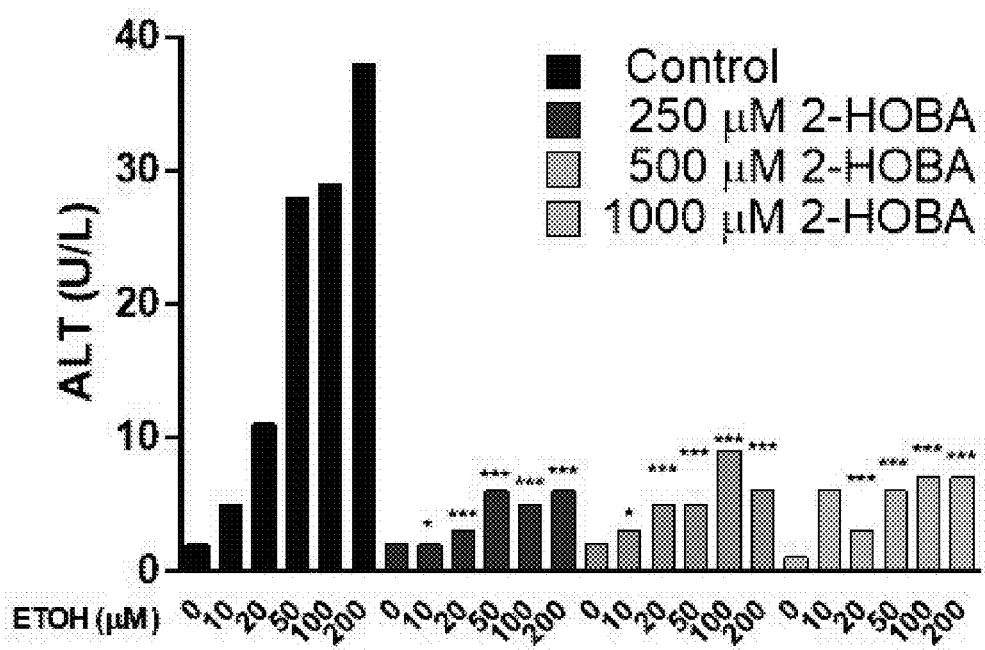
FIG. 5A depicts ALT and FIG. 5B depicts AST levels in the media of HepaRG cells pretreated with different levels of 2-HOBA.
Figure 5B:
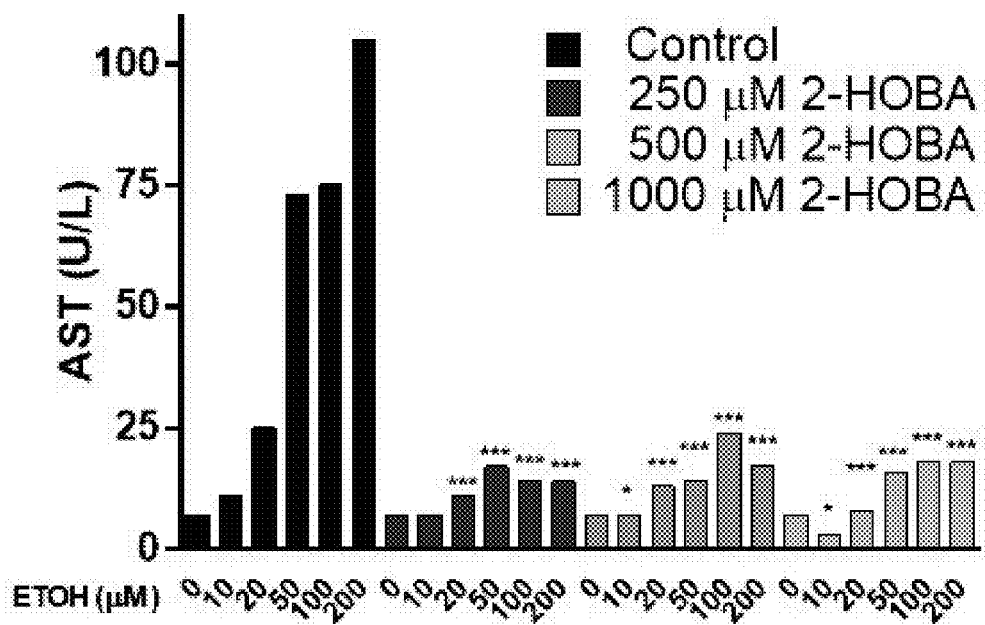
Figure 6:
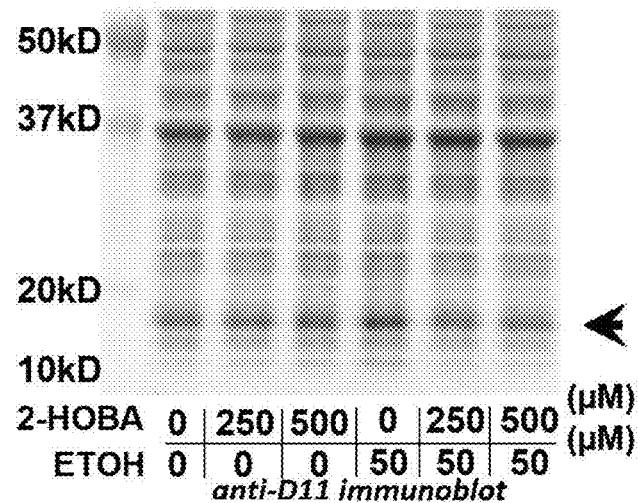
FIG. 6 shows the effects of 2-HOBA pretreatment against ethanol-mediated γ-KA formation.
Figures 7A, 7B:
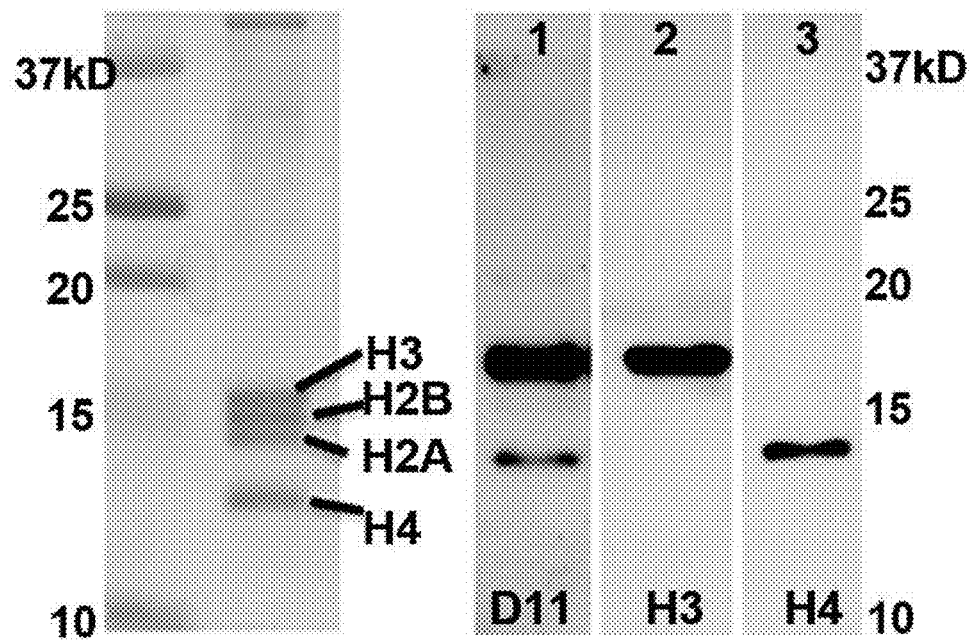
FIG. 7A shows the identification of γ-KA-modified histone-H3 and -H4 in mouse lung and FIG. 7B shows an immunoblot of isolated histones.
Figure 8A:
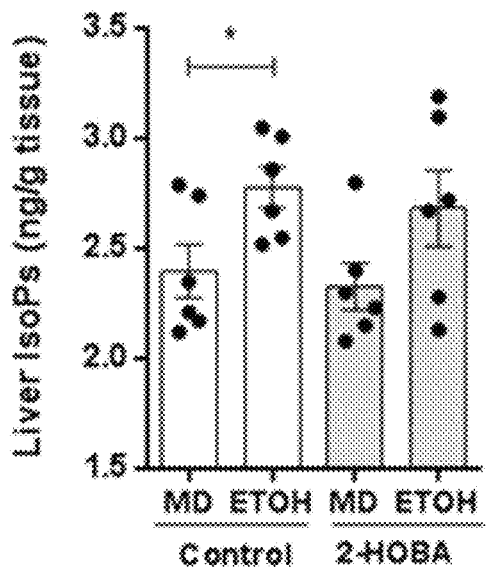
FIG. 8A is a graph depicting liver isoprostanes (IsoP) in mice where the efficacy of 2-HOBA was tested.
Figure 8B:
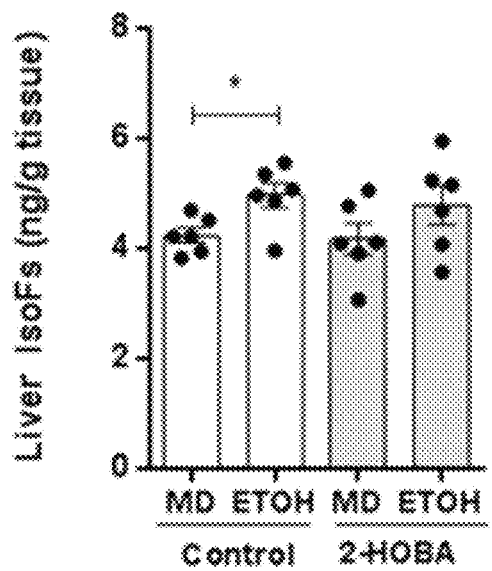
FIG. 8B is a graph depicting liver isofurans (IsoF) in mice where the efficacy of 2-HOB was tested.
Figure 8C:
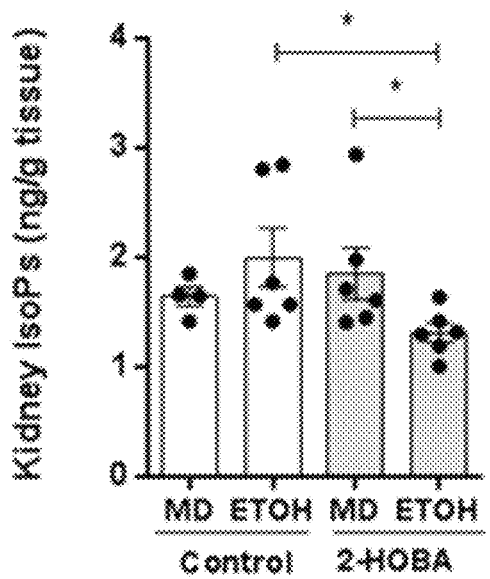
FIG. 8C is a graph depicting kidney isoprostanes (IsoP) in mice where the efficacy of 2-HOBA was tested.
Figure 8D:
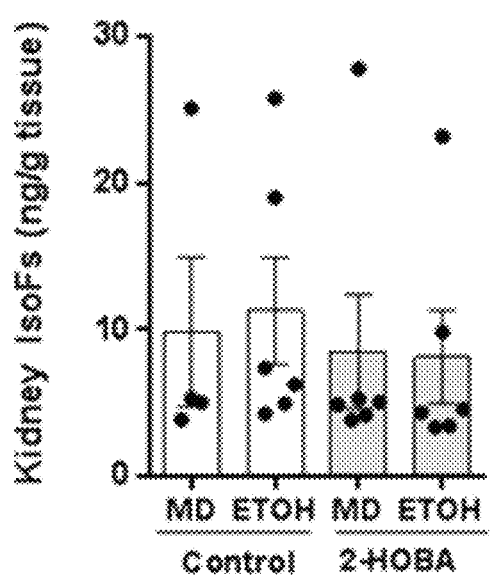
FIG. 8D is a graph depicting kidney isofurans (IsoF) in mic where the efficacy of 2-HOBA was tested.
Figure 9A:
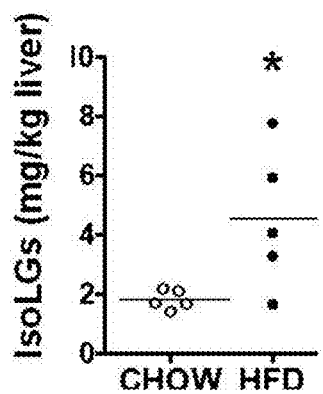
FIG. 9A depicts IsoLG formation in the livers of mice fed a high fat diet.
Figure 9B:
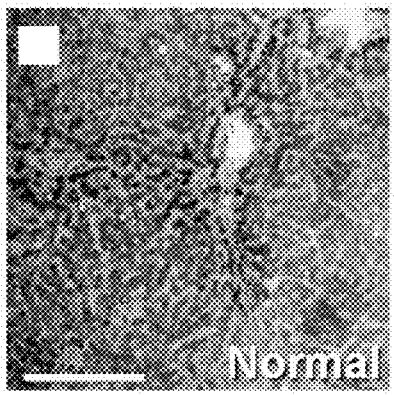
FIG. 9B shows IsoLG staining on normal livers.
Figure 9C:
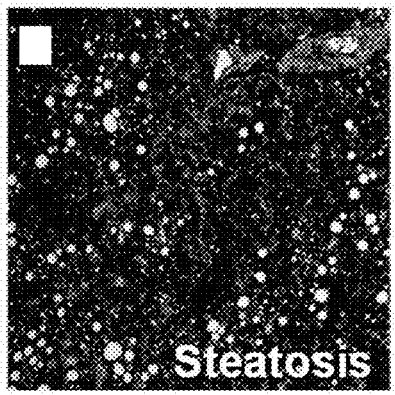
FIG. 9C depicts IsoLG staining on steatosis livers.
Figure 9D:
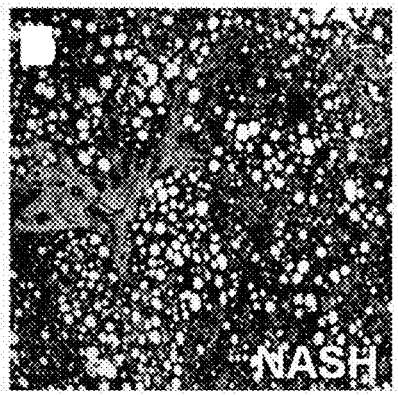
FIG. 9D shows IsoLG staining on NASH livers.

Fully-differentiated, 21-day, HepaRG hepatocytes (BioPredict International) display clear epithelial cells surrounded by hepatocyte colonies that contain numerous bile canaliculi which readily metabolize the fluorescent MRP2 substrate, CDFDA. HepaRG cells are a unique and well-established human hepatic cell culture system with high fidelity to the absorption, distribution, metabolism, and excretion of human liver. Consistent with the known mechanisms of action of 2-HOBA, a 24 hr pre-treatment of HepaRG cells with 2-HOBA (0, 250, 500 and 1000 µM) was followed by increasing ethanol concentration (0-200 mM; 24 hr) but did not affect reactive oxygen species formation (FIG. 4A). However, 2-HOBA almost completely prevented cell death by ethanol (FIG. 4B). Similarly, a 24 hr pre-treatment of HepaRG cells with 2-HOBA (0, 250, 500 and 1000 µM) followed by increasing ethanol concentration (0-200 mM; 24 hr) resulted in a near normalization of ALT (FIG. 5A) and AST (FIG. 5B) levels in culture media taken from HepaRG hepatocytes. Currently, there is little knowledge concerning the identity of proteins that are susceptible to γ-KAs modification. The present inventors investigated the identity of proteins adducted endogenously using cultured HepaRG hepatocytes, exposed to ethanol with or without prior 2-HOBA pretreatment (0, 250 or 500 µM for 24 hr). Cells were harvested and total protein was resolved by SDS-PAGE then probed with a well-characterized single chain antibody, D11 SCFv, which recognizes peptides and proteins modified by γ-KAs isomers (FIG. 6). Consistent with the theory that there is a 'pool' of γ-KA-modification susceptible proteins, all treatments exhibited a similar level of "background" anti-D11 cross-reactivity; however, there was a robust increase in the cross-reactivity of a single band (arrow) at ~18 kD in hepatocytes treated with ethanol but without 2-HOBA protection. In contrast, the intensity of this band was restored to levels observed in untreated controls with 2-HOBA pre-treatment 2-HOBA (250 or 500 µM). Interestingly, this band is of the same molecular weight as that recently identified as γ-KA adducted and anti-D11 antibody in a mouse model of lung fibrosis (FIG. 7). These data signify that ETOH promotes the formation of γ-KA-adducted proteins, the formation of which can be blocked with 2-HOBA.

Taken together, these findings demonstrate that γ-KAs are major mediators of liver injury caused by lipid peroxidation, and that the use of 2-HOBA protects against cell death induced by such oxidants or ethanol exposure. Targeting γ-KAs may be used as a method for preventing lipid peroxidation and the resulting γ-KA-specific immune responses in alcoholic liver disease.

Example 2

2-HOBA and ethanol were concurrently administered to $C_{57}$/BL6J mice to establish the efficacy of 2-HOBA in mitigating ethanol-mediated liver dysfunction (increased AST and ALT), reducing γ-KA formation, favorably altering immune responses and stimulating beneficial intracellular signaling pathways. The results indicate that pre-treatment with 2-HOBA (1.0 mg/ml) significantly reduces liver injury (elevated γ-KAs and liver function enzymes) activated upon ethanol exposure. 2-HOBA (0.5 g/L in Lieber-DeCarli liquid diet, LDLD) was administered to mice prior to ethanol treatment for 14 days to examine 2-HOBA efficacy in mitigating liver injury. Ethanol (5% v/v) was administered using the NIAAA model (10 days ethanol in LDLD+binge). Food intake and body weight were not significantly impacted with the addition of 0.5 g/L of 2-HOBA to LDLD (data not shown). White blood cell and lymphocyte cell counts were reduced while eosinophil and basophil counts were increased with ethanol relative to maltodextrin feeding (Table 1), consistent with other reports of alcoholic liver injury. Such responses were not observed in the presence of 2-HOBA. 2-HOBA at 0.5 g/L did not attenuate increases in serum AST or ALT in these studies (Table 2).

TABLE 1

Clinical blood chemistry of mice after the NIAAA ethanol treatment regimen.

|  | Con + MD | Con + ETOH | 2-HOBA + MD | 2-HOBA + ETOH |
| --- | --- | --- | --- | --- |
| WBC | 5.70 ± 0.61 | 2.47 ± 0.33** | 6.08 ± 1.05 | 3.11 ± 0.66 |
| Lymphocytes | 65.67 ± 2.63 | 50.18 ± 2.98** | 58.14 ± 5.45 | 50.42 ± 4.59 |
| Monocytes | 7.97 ± 0.65 | 8.29 ± 1.32 | 6.66 ± 0.92 | 6.33 ± 1.11 |

TABLE 1-continued

Clinical blood chemistry of mice after the NIAAA ethanol treatment regimen.

|  | Con + MD | Con + ETOH | 2-HOBA + MD | 2-HOBA + ETOH |
|---|---|---|---|---|
| Eosinophils | 0.96 ± 0.16 | 3.61 ± 0.69*** | 1.79 ± 0.40 | 2.71 ± 0.46 |
| Basophils | 0.40 ± 0.10 | 1.74 ± 0.66* | 0.60 ± 0.14 | 1.27 ± 0.26# |

Abbreviations: Cell counts are in (x10³/μl). WBC; white blood count; Statistical significance was determined using a two-tailed unpaired Student's t-test. N = 12 mice per group. P ≤ 0.01 vs Con + MD; ***P ≤ 0.001 vs Con + MD; #P ≤ 0.05 vs 2-HOBA + MD.

TABLE 2

Primary endpoints in mice after the NIAAA treatment regimen with or without 2-HOBA (0.5 g/L).

| | (1) Con + MD | (2) Con + ETOH | (3) 2-HOBA + MD | (4) 2-HOBA + ETOH | 1 vs 2 | 3 vs 4 | 1 vs 3 | 2 vs 4 |
|---|---|---|---|---|---|---|---|---|
| AST | 992.8 ± 345.1 | 961.1 ± 297.7 | 566.5 ± 34.1 | 1725.0 ± 300.2 | 0.93 | 0.0017*** | 0.34 | 0.98 |
| ALT | 77.2 ± 15.1 | 406.4 ± 77.2 | 54.3 ± 20.1 | 443.7 ± 66.2 | 0.0018** | <0.0001*** | 0.29 | 0.75 |

Data reported as mean ± S.E.M.
AST, serum aspartate aminotransferase;
ALT, alanine aminotransferase;
N = 12 mice per group.
**P indicates significance ≤ 0.01,
***P indicates significance ≤ 0.001 by unpaired Student's two-tailed t-test. AST and ALT are in U/L.

An additional cohort of mice were administered a 14-day pretreatment of 2-HOBA (1.0 g/L) prior to administration of ethanol using the NIAAA model. Mice administered ethanol consumed less food and consequently weighed ~2.5 g less than maltodextrin-fed controls at the end of study.

TABLE 3

Primary endpoints in mice the NIAAA treatment regimen with or without 2-HOBA (1.0 g/L).

| | (1) Con + MD | (2) Con + ETOH | (3) 2-HOBA + MD | (4) 2-HOBA + ETOH | 1 vs 2 | 3 vs 4 | 1 vs 3 | 2 vs 4 |
|---|---|---|---|---|---|---|---|---|
| AST | 634.4 ± 95.0 | 906.1 ± 186.1 | 693.6 ± 173.1 | 676.6 ± 86.7 | 0.17 | 0.94 | 0.76 | 0.30 |
| ALT | 50.2 ± 5.5 | 253.9 ± 62.9 | 127.5 ± 78.59 | 164.4 ± 20.8 | 0.0014*** | 0.72 | 0.35 | 0.21 |
| BUN | 21.3 ± 1.2 | 27.1 ± 5.5 | 34.6 ± 2.9 | 22.6 ± 1.7 | 0.25 | 0.60 | 0.30 | 0.47 |
| CRE | 0.4 ± 0.01 | 0.2 ± 0.05 | 0.3 ± 0.05 | 0.3 ± 0.04 | 0.0003*** | 0.67 | 0.19 | 0.06 |

Data reported as mean ± S.E.M.
AST, serum aspartate aminotransferase;
ALT, alanine aminotransferase;
N = 12 mice per group.
***P indicates significance ≤ 0.001 by unpaired Student's two-tailed t-test. AST and ALT concentrations are in U/L. Blood urea nitrogen (BUN) and creatinine (CRE) units are mg/dL.

Hepatic triglyceride content trended to be lower in ETOH-challenged mice pre-treated with 2-HOBA (1.0 g/L)). Liver damage as indicated by changes in serum ALT trended lower with 2-HOBA pre-treatment (164.4±20.8 U/L) versus Con+ETOH mice vs (253.0±62.9 U/L) but these did not reach statistical significance. AST was lower in mice pretreated with 2-HOBA+ETOH (676.6±86.7 U/L) compared to controls (906.1±186.1 U/L) but these did not reach statistical significance. These changes were accompanied with significant reductions in hepatic isoprostanes (IsoP) and isofurans (IsoF) and also resulted in significant reductions in kidney isoprostane levels (1.3±0.1 ng/g versus 2.0±0.3 ng/g in Con+ETOH; P<0.05) as shown in FIG. 8.

Pre-treatment with 2-HOBA for 14 days at 1.0 g/L in the NIAAA model reduced liver injury and ameliorated the significant increases in hepatic isoprostane and isofuran content observed with ETOH exposure and additionally decreased kidney isoprostane formation.

Figure 10A:
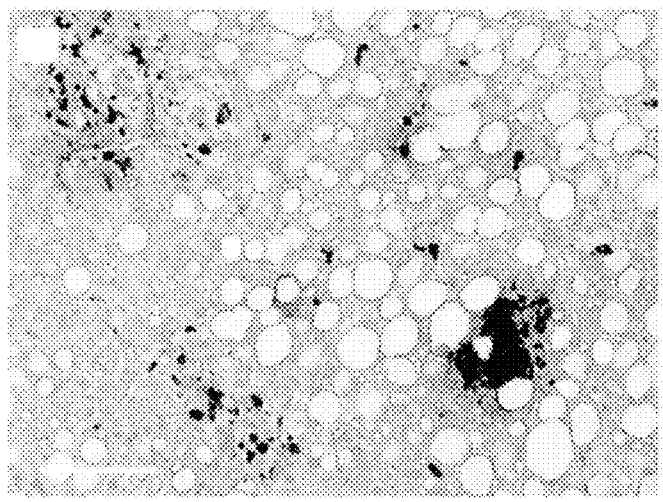
FIG. 10A depicts neutrophil staining in NASH human liver.
Figure 10B:
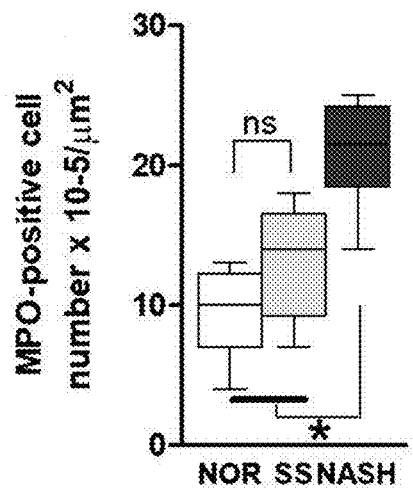
FIG. 10B is a graph showing MPO-positive cells in NASH livers compared to normal or SS specimens.
Figure 12A:
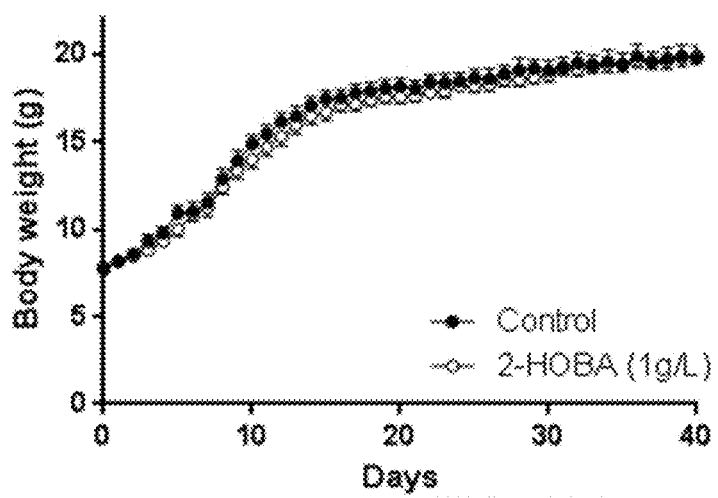
FIGS. 12A-12T compare the effects of administering 2-HOBA to STAM mice v. control mice.
Figure 12A:
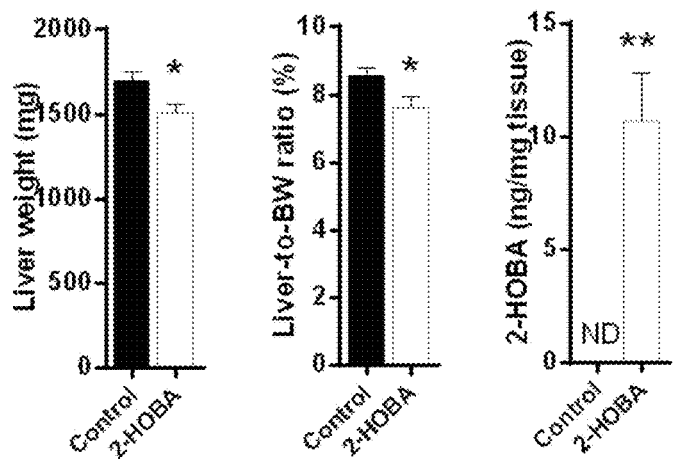
Figure 12A:
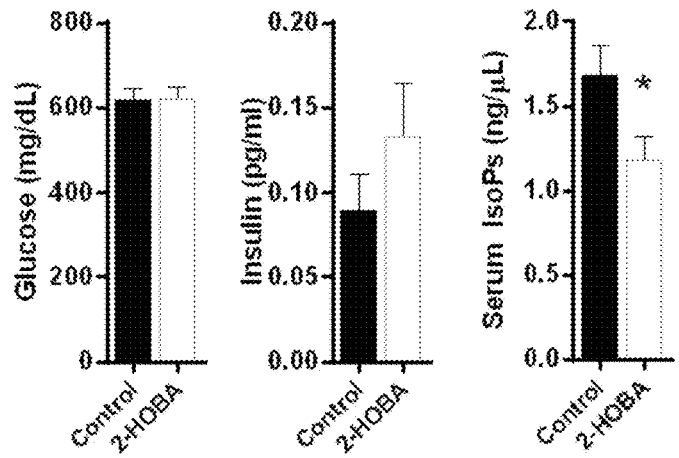
Figure 12M:
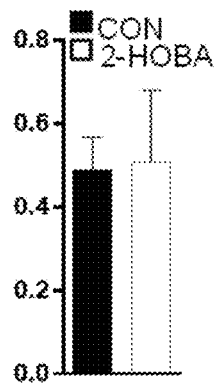
Figure 12N:
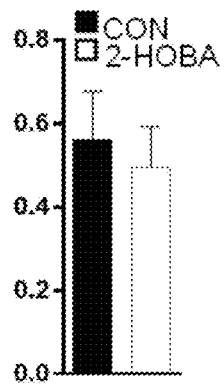
Figure 12O:
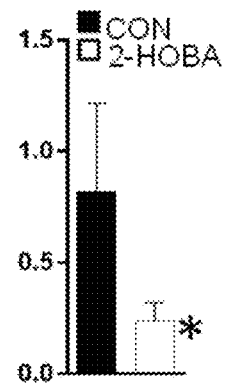
Figure 12P:
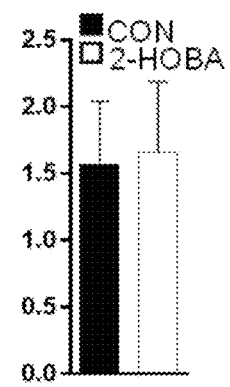
Figure 12Q:
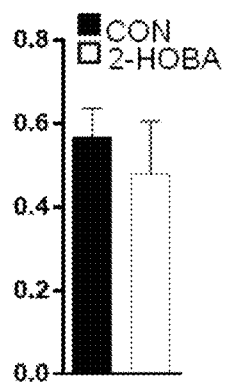
Figure 12R:
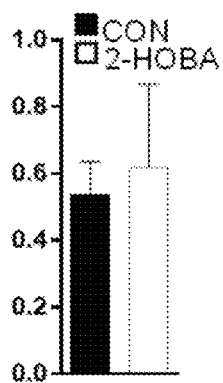
Figure 12S:
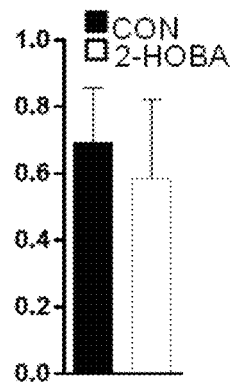
Figure 12T:
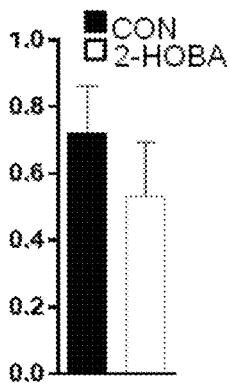

Example 3-NASH $F_2$-Isoprostanes ($F_2$—IsoPs) are prostaglandin-like compounds formed in vivo via a non-enzymatic mechanism involving the free radical-initiated peroxidation of arachidonic acid and have been shown to be the most accurate predictors of oxidative stress in vivo. Elevated levels of plasma or urinary $F_2$-IsoPs have been reported in alcoholic liver disease patients and in animals with NAFLD/NASH and increased liver $F_2$-IsoP also have been reported in humans and animals with NASH. $F_2$-IsoPs values are also increased in chronic hepatitis. Preliminary data show that liver obtained from mice and human liver tissue with proven NAFLD/NASH show dramatically increased levels of IsoLG protein adducts relative to controls (FIG. 9). These observations were concurrent with increased myeloperoxidase-positive neutrophil staining in specimens that is hallmark of biopsy-proven NASH (FIG. 10), suggestive of enhanced inflammation. Several agents appear to be associated with this enhanced inflammatory process.

It has been demonstrated that increased plasma lipopolysaccharide (LPS) and Free Fatty Acids (FFAs) in plasma of NASH patients which were associated with increased hepatic TLR4-Myd88-independent signaling. It has also demonstrated in cultured HepaRG cells that palmitate and LPS induce NF-kB activity that can be blocked with chemical- or small-interfering RNA-mediated inhibition of TLR4. Liang et al recently demonstrated that alternative metabolic ligands (cholesterol and carbohydrate) also may trigger enhanced steatosis, hepatocellular hypertrophy, and mixed-type (neutrophilis and mononuclear cell) inflammation through an inflammasome-mediated mechanism.

Inflammasomes are multimeric protein complexes of the innate immune system that upon PAMP (pathogen-associated molecular pattern) or DAMP (damage-associated molecular pattern) binding, either directly or through the adaptor molecule ASC, activating caspase 1. Caspase 1 in turn activates downstream signaling pathways and the resultant changes in biological function vary considerably depending upon cell type and initiating ligand. Inflammasomes are activated by members of the (NOD)-like receptor (NLR) family (NLRP1-3, NLRP6-7, NLRP12, NLRC4), NAIP and Aim2. Activation of the NLRP3 inflammasome leads to caspase-1 cleavage of inactive pro-IL-1β, pro-IL-18 and pro-IL-33 into their active forms. Fatty acids, cholesterol, and protein aggregates are among the known NLRP3-inflammasome activators. The described molecular triggers of NASH inflammasomes include DNA, saturated fatty acids and LPS, NLRP-1. This suggests that IsoLGs are also additional potent inflammasome activators through mechanisms that are not fully delineated. Indeed, defective NLRP1- and NLRP3-signaling/activation by IsoLG ligands may underpin altered liver immunometabolism, host gut microbiome adaptations, and defective NLRP-inflammasome sensing that are hallmark of the NAFL to NASH transition.

: 2-Hydroxybenzylamine (2-HOBA) is 980 times more reactive than lysine with γKAs and importantly, does not inhibit cyclooxygenase enzymes. In a model of oxidant mediated cell death 2-HOBA almost completely prevented hepatocyte cell death induced by t-butylhydroperoxide (tBHP). This is a remarkable finding given the fact the pathogenesis of oxidative injury is quite complex and multifaceted. In addition, it was demonstrated that 2-HOBA has a protective effect against oxidant mediated cell death in HepG2 cells exposed to varying concentrations of $H_2O_2$. Taken together, these findings suggest that γKAs are potentially major mediators of liver injury caused by lipid peroxidation, and that the use of 2-HOBA would protect against cell death induced by such oxidants in the liver. Obviously, the efficacy of 2-HOBA depends on its accumulation in target tissues, and this was recently supported by pharmacokinetic studies in an in vivo mouse model. Administration of 2-HOBA at 1, 3, and 10 g/L for 7 days was associated with dose-dependent increases in plasma and liver levels of 2-HOBA. The levels in the liver were about 10 times higher than in plasma.

One model used in studying the pathogenesis of NASH, cirrhosis and HCC is the STAM model, (Stelic Inc. Tokyo, Japan). With strong fidelity to human NASH both histologically and physiologically (elevated fasting blood sugar, liver biochemistries, intrahepatic lipid, dyslipidemia; FIG. 11), the STAM model develops the features previously difficult to obtain in genetic knockouts or dietary models of NAFLD. The present inventors have demonstrated that 2-HOBA can reduce NAFLD severity in STAM mice (FIG. 12).

In the STAM™ model, NASH is induced in $C_{57}BL/6$ mice by a single subcutaneous injection of 200 g streptozotocin (STX) solution 2 days after birth and feeding with high-fat diet beginning at 4 wks of age. At 3 wks of age, 12 mice that had undergone STZ injection were divided into two groups: 1) 2-HOBA (n=6), and 2) vehicle control (n=6). Mice in the 2-HOBA group received 2-HOBA in drinking water (1 g/L water), while the vehicle control group received plain water without 2-HOBA. At 4 wks of age, all mice were placed on ad libitum high fat diet. All mice remained on the high fat diet and received 2-HOBA-supplemented or plain water based on their group assignment throughout the study protocol. Body weights and food/water intake were monitored weekly. Animals were sacrificed at 9 wks of age (6 weeks of 2-HOBA or vehicle treatment), and tissues and serum were collected for analysis.

Liver sections were stained with hematoxylin and eosin (for scoring of steatosis, hepatocyte ballooning, and inflammation), Sirius red (for assessment of fibrosis), and for $F_{4/80}$+macrophages. Scoring was performed in a blinded manner for steatosis, ballooning, inflammation, and necrosis using the following criteria, Steatosis (0-4): 0=<5%; 1=5-25%; 2=25-50%; 3=50-75%; 4=75-100%. Ballooning (0-3): 0=absent; 1=mild (focal involving fewer than three hepatocytes); 2=moderate (focal involving more than three hepatocytes or multifocal); 3=prominent (multifocal with more than two foci of three or more hepatocytes). Inflammation (0-4): 0=absent; 1=minimal (zero to one focus per 20× field); 2=mild (two foci); 3=moderate (three foci); 4=severe (four or more foci). Serum levels of glucose, insulin, alanine transaminase, aspartate transaminase, triglycerides, cholesterol, and $F_2$-isoprostanes were measured. Serum and tissue levels of the following inflammatory markers were measured by multiplex assay (Luminex, Millipore, Billerica, MA): IL1α, IL-6, IL-1β, IL-10, IL-17, MCP-1, and TNFα. Liver 2-HOBA, $F_2$-isoprostane, and isofuran levels were determined by LC/MS/MS methods. Liver mRNA expression was assessed via RT-qPCR for the following genes: Gck, Pck1, Pdk4, Irs1, Irs2, Pgc1a, Cpt1a, Gyk, Srepb1c, Acc1, Fxr, Cox1, Cox2, Nox4, Catalase, Gpx1, Gp41phx, and p22phox. Liver protein content and phosphorylation status were determined for Akt, GSK30, mTOR, ERK, JNK, FOXO1, and NALP. Two-tailed independent samples t-tests were used to compare endpoints between 2-HOBA and vehicle treated groups. Significance was set at α=0.05.

The viability, clinical signs and behavior were monitored daily. Mean body weights and food intake were similar between groups, however liver weight, and liver to body weight ratios were significantly reduced (FIG. 12). Serum glucose levels were similar between groups, but insulin, ALT and lipids all were trending towards reduction. Importantly, serum isoprostanes (a marker of BFE formation and IsoLG adduction) and histologic NASH severity were significantly reduced with 2-HOBA treatment.

Figure 13A:
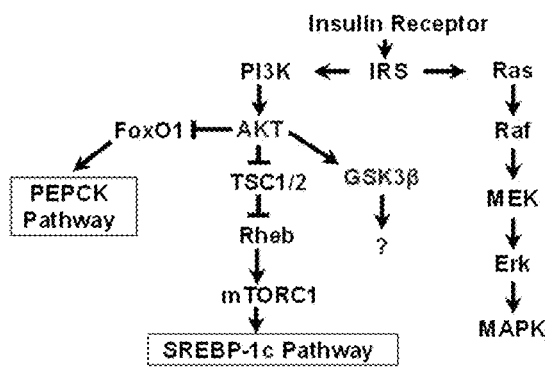
FIG. 13A-F shows insulin signaling and hepatic inflammasomes in STAM™ mice.
Figure 13B:
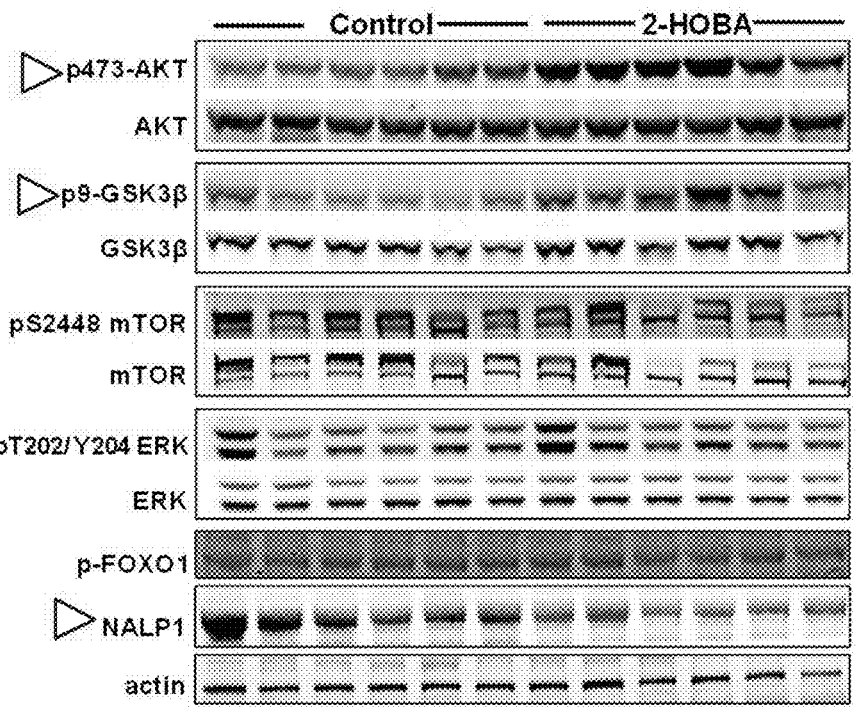
Figures 13C, 13D, 13E, 13F:
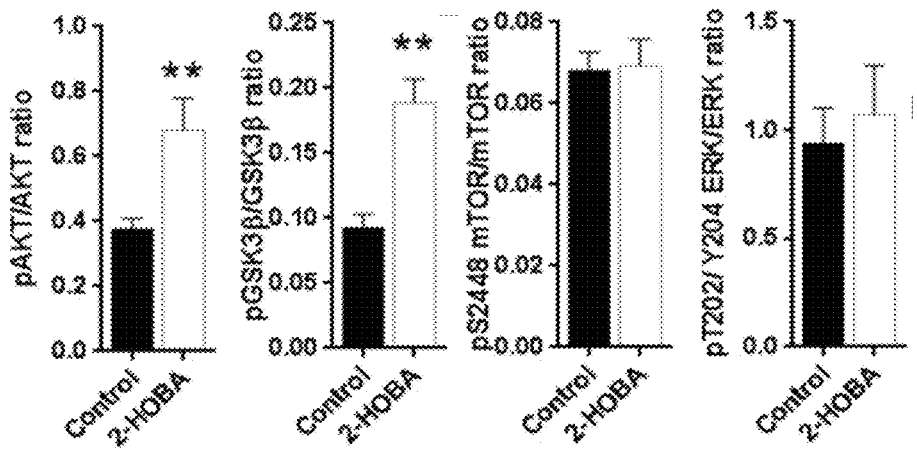
Figure 15A:
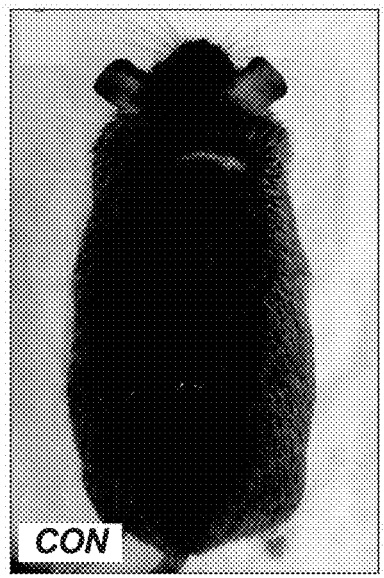
Figure 15B:
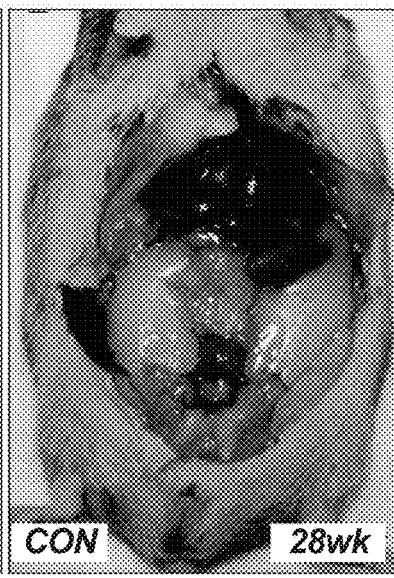
Figure 15C:
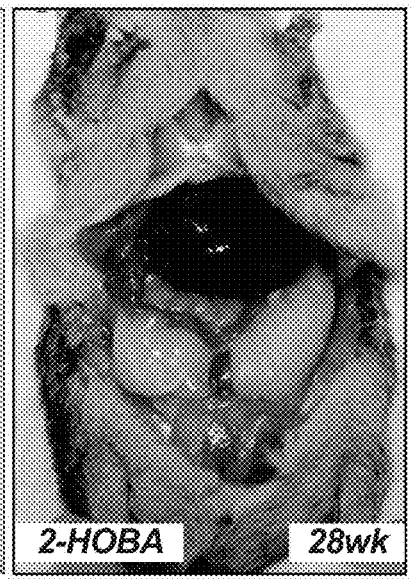
Figure 15D:
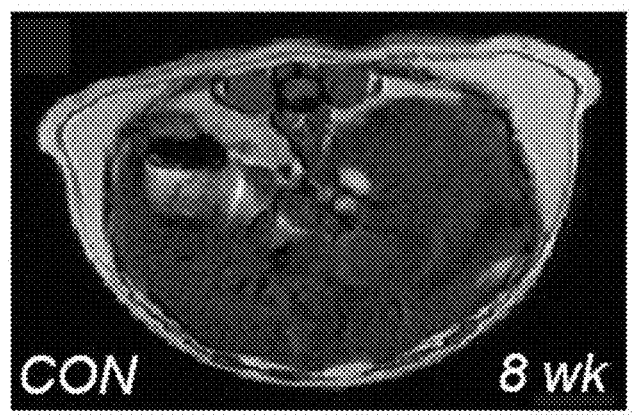
Figure 15E:
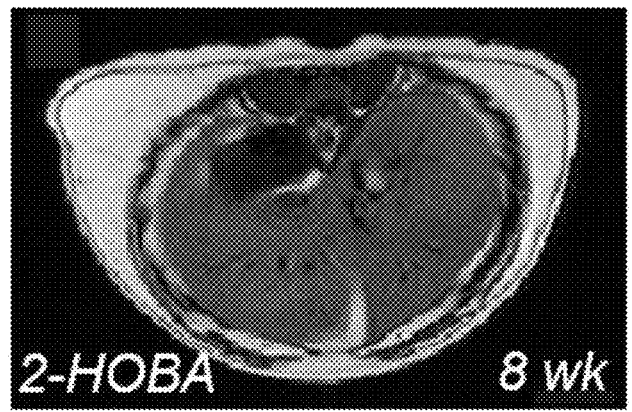
Figure 15F:
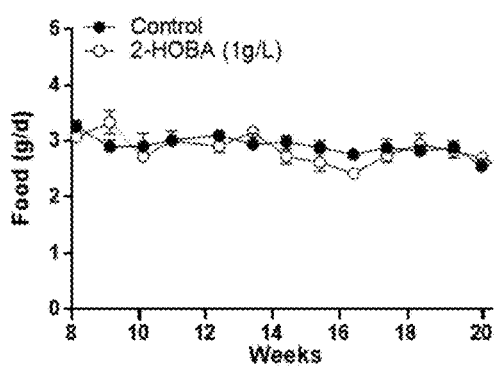
Figure 15G:
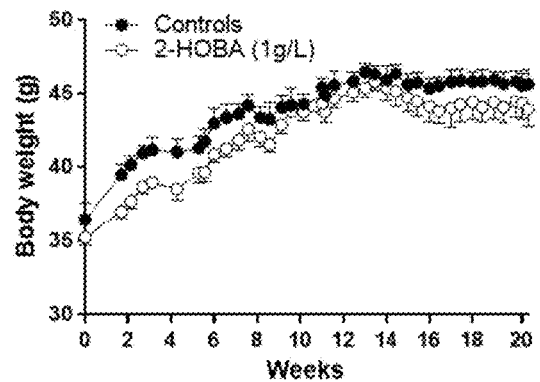
Figure 15H:
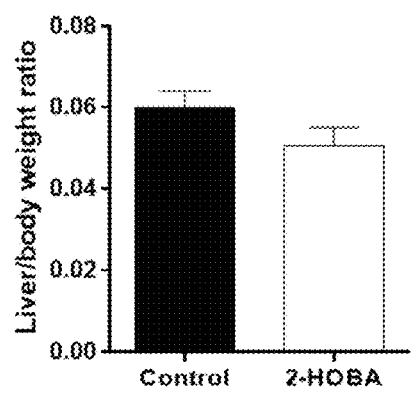
Figure 15I:
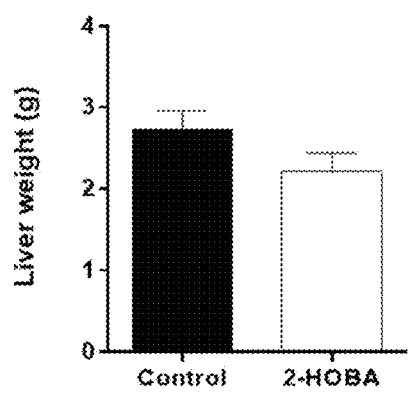
Figure 15J:
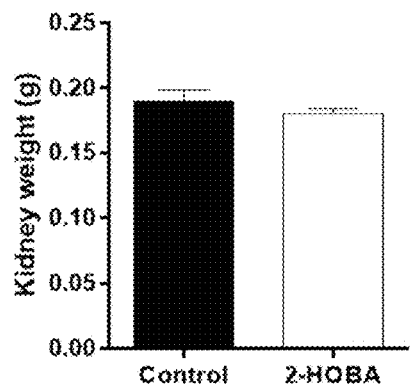
Figure 15K:
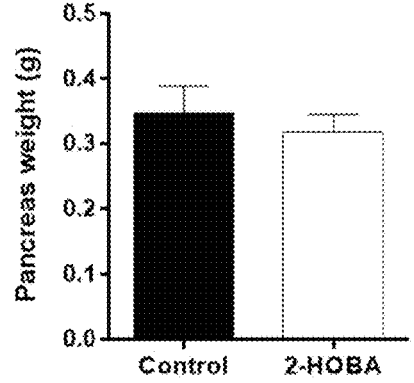
Figure 16H:
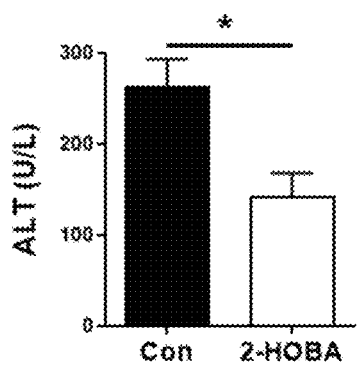
FIG. 16A-N summarizes results of DIAMOND™ mice testing.
Figure 16I:
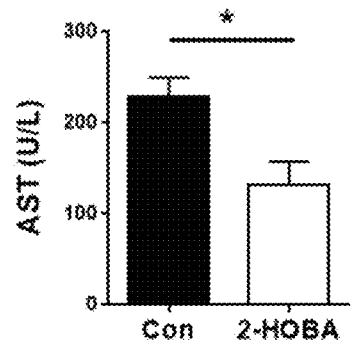
Figure 16J:
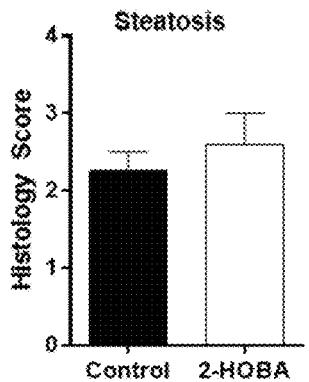
Figure 16K:
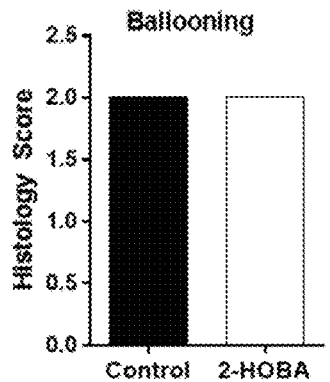
Figure 16L:
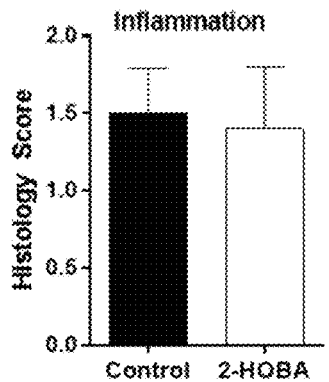
Figure 16M:
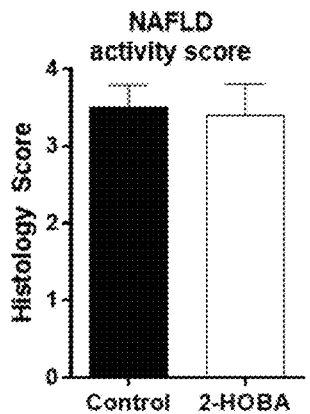
Figure 16N:
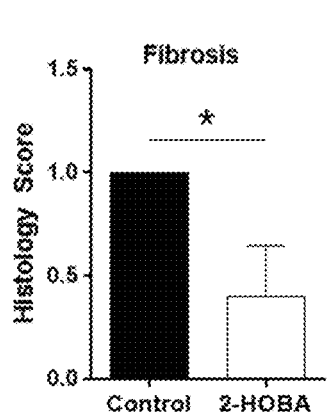

The livers from STAM mice were subjected to immunoblot analysis to better understand the basis for the improvements in liver function and phenotypes described in FIG. 13. 2-HOBA treatment dramatically increased AKT and GSK30 phosphorylation without significantly altering signaling through mTOR, ERK or FOXO1. In addition, the data show significantly decreased expression of pyruvate dehydrogenase kinase 4 (pdk4), a key protein in the regulation of mitochondrial fuel metabolism, suggesting that the reductions in liver weight, improvements in NASH severity and reductions in serum isoprostanes with 2-HOBA treatment may be mediated by an γKA-mediated mechanism affecting mitochondria function. Furthermore, the data show a decrease NALP1 with 2HOBA treatment. A role for NRLP3-inflammasomes in regulating mitochondrial function was recently described.

These data in the STAM model signify that IsoLG-protein adducts cause injury to the liver, and that 2-HOBA potently reduces NASH severity and restores markers of hepatic insulin sensitivity. Importantly, the data show NLRP1-inflammasome activation in this model is blocked with oral 2-HOBA administration suggesting a role for 2-HOBA in blocking IsoLG-mediated inflammasome NASH responses.

Example 4

DIAMOND (Diet Induced Animal Model of Non-alcoholic fatty liver Disease) is a proprietary isogenic mouse strain that sequentially develops non-alcoholic fatty liver disease, non-alcoholic steatohepatitis, fibrosis, and hepatocellular carcinoma in response to a high-fat, high-sugar diet. Disease progression in the DIAMOND mice uniquely parallels human disease progression, including histopathology. The DIAMOND mouse model is unique in that it is the only murine model of NAFLD/NASH that develops NASH solely as a result of the Western diet (high fat, sugar water) with no gene knockouts or toxins to induce liver pathology (FIG. 14).

Twelve 8-wk old male DIAMOND mice were placed on ad libitum high fat diet (Harlan—ENVIGO TD.88317) and water containing glucose (18.9% w/v) and fructose (23.1% w/v); all mice remained on this diet throughout the study protocol. At 12 wks of age, mice were divided into two groups: 1) 2-HOBA (n=6), and 2) vehicle controls (n=6). Animals in the 2-HOBA group received 2-HOBA in drinking water (1 g/L water with glucose and fructose). The vehicle control group received water without 2-HOBA (with glucose and fructose). Body weight and food intake were measured weekly. At ~23 wks of age, all animals underwent a glucose tolerance test (GTT) and MRI imaging to assess hepatic fat. For the GTT, animals were fasted for 12 hours and then glucose (2 g/kg bw of a 100 mg/mL glucose in sterile water) was administered by oral gavage. Blood was sampled at 0, 15, 30, 45, 60, 90, and 120 minutes after glucose administration and area under the curve was calculated. Animals were sacrificed at 24 wks of age (12 weeks of 2-HOBA or vehicle treatment). Tissues and serum were collected for analysis.

Liver sections were stained with hematoxylin and eosin (for scoring of steatosis, hepatocyte ballooning, and inflammation) and Sirius red (for assessment of fibrosis). Scoring was performed in a blinded manner for steatosis, ballooning, inflammation, and necrosis using the following criteria, Steatosis (0-4): 0=<5%; 1=5-25%; 2=25-50%; 3=50-75%; 4=75-100%. Ballooning (0-3): 0=absent; 1=mild (focal involving fewer than three hepatocytes); 2=moderate (focal involving more than three hepatocytes or multifocal); 3=prominent (multifocal with more than two foci of three or more hepatocytes). Inflammation (0-4): 0=absent; 1=minimal (zero to one focus per 20× field); 2=mild (two foci); 3=moderate (three foci); 4=severe (four or more foci). Serum levels of glucose, alanine transaminase, and aspartate transaminase were measured. Liver mRNA expression was assessed via RT-qPCR for the following genes: Tnfa, Nlrp1a, Il1b, Il18, Timp1, Col1a1, ProCard, Nlrp3, Casp1, ProIl1b, Tgfb1, Bambi, Pdk4, and Gapdh. Two-tailed independent samples t-tests were used to compare endpoints between 2-HOBA and vehicle treated groups. Significance was set at α=0.05.

FIGS. 15-16 summarizes the results of the DIAMOND mice testing. These data demonstrate a trend for a reduction in liver weight which was accompanied a significant reduction in the liver enzymes ALT and AST with 2HOBA supplementation. These findings support the efficacy of 2-HOBA to prevent the development or attenuate the severity of NASH.

REFERENCE LIST

Albano E, Vidali M. Immune mechanisms in alcoholic liver disease. Genes Nutr 2010; 5(2):141-147.PM:19809845

Mottaran E, Stewart S F, Rolla R et al. Lipid peroxidation contributes to immune reactions associated with alcoholic liver disease. Free Radic Biol Med 2002; 32(1):38-45.PM:11755315

Stewart S F, Vidali M, Day C P, Albano E, Jones D E. Oxidative stress as a trigger for cellular immune responses in patients with alcoholic liver disease. Hepatology 2004; 39(1):197-203.PM:14752838

Lee G S, Yan J S, Ng R K, Kakar S, Maher J J. Polyunsaturated fat in the methionine-choline-deficient diet influences hepatic inflammation but not hepatocellular injury. J Lipid Res 2007; 48(8):1885-1896.PM:17526933

1. Williams R. The pervading influence of alcoholic liver disease in hepatology. Alcohol Alcohol 2008; 43(4):393-397.PM:18385413
2. Murray C J, Richards M A, Newton J N et al. UK health performance: findings of the Global Burden of Disease Study 2010. Lancet 2013; 381(9871):997-1020.PM:23668584
3. Basra S, Anand B S. Definition, epidemiology and magnitude of alcoholic hepatitis. World J Hepatol 2011; 3(5):108-113.PM:21731902
4. Mackie J, Groves K, Hoyle A et al. Orthotopic liver transplantation for alcoholic liver disease: a retrospective analysis of survival, recidivism, and risk factors predisposing to recidivism. Liver Transpl 2001; 7(5):418-427.PM:11349262
5. Miguet M, Monnet E, Vanlemmens C et al. Predictive factors of alcohol relapse after orthotopic liver transplantation for alcoholic liver disease. Gastroenterol Clin Biol 2004; 28(10 Pt 1):845-851.PM:15523219
6. Miller W R, Walters S T, Bennett M E. How effective is alcoholism treatment in the United States?J Stud Alcohol 2001; 62(2):211-220.PM:11327187
7. O'Shea R S, Dasarathy S, McCullough A J. Alcoholic liver disease. Hepatology 2010; 51(1):307-328.PM:20034030
8. Wang H J, Gao B, Zakhari S, Nagy L E. Inflammation in alcoholic liver disease. Annu Rev Nutr 2012; 32:343-368.PM:22524187
9. Roychowdhury S, McMullen M R, Pritchard M T et al. An early complement-dependent and TLR-4-independent phase in the pathogenesis of ethanol-induced liver injury in mice. Hepatology 2009; 49(4):1326-1334.PM:19133650
10. Cohen J I, Roychowdhury S, McMullen M R, Stavitsky A B, Nagy L E. Complement and alcoholic liver disease: role of C1q in the pathogenesis of ethanol-induced liver injury in mice. Gastroenterology 2010; 139(2):664-74, 674.PM:20416309
11. Pritchard M T, McMullen M R, Medof M E, Stavitsky A, Nagy L E. Role of complement in ethanol-induced liver injury. Adv Exp Med Biol 2008; 632:175-186.PM:19025122
12. Gao B, Bataller R. Alcoholic liver disease: pathogenesis and new therapeutic targets. Gastroenterology 2011; 141(5):1572-1585.PM:21920463

13. Lieber C S. Alcoholic fatty liver: its pathogenesis and mechanism of progression to inflammation and fibrosis. Alcohol 2004; 34(1):9-19.PM:15670660
14. Rouach H, Fataccioli V, Gentil M, French S W, Morimoto M, Nordmann R. Effect of chronic ethanol feeding on lipid peroxidation and protein oxidation in relation to liver pathology. Hepatology 1997; 25(2):351-355.PM:9021946
15. Seki S, Kitada T, Yamada T, Sakaguchi H, Nakatani K, Wakasa K. In situ detection of lipid peroxidation and oxidative DNA damage in non-alcoholic fatty liver diseases. J Hepatol 2002; 37(1):56-62.PM:12076862
16. Benedetti A, Comporti M, Esterbauer H. Identification of 4-hydroxynonenal as a cytotoxic product originating from the peroxidation of liver microsomal lipids. Biochim Biophys Acta 1980; 620(2):281-296.PM:6254573
17. Janero D R. Malondialdehyde and thiobarbituric acid-reactivity as diagnostic indices of lipid peroxidation and peroxidative tissue injury. Free Radic Biol Med 1990; 9(6):515-540.PM:2079232
18. Morrow J D, Awad J A, Boss H J, Blair I A, Roberts L J. Non-cyclooxygenase-derived prostanoids ($F_2$-isoprostanes) are formed in situ on phospholipids. Proc Natl Acad Sci USA 1992; 89(22):10721-10725.PM:1438268
19. Roychowdhury S, McMullen M R, Pritchard M T, Li W, Salomon R G, Nagy L E. Formation of gamma-ketoaldehyde-protein adducts during ethanol-induced liver injury in mice. Free Radic Biol Med 2009; 47(11):1526-1538.PM:19616618
20. Morrow J D, Hill K E, Burk R F, Nammour™, Badr K F, Roberts II. A series of prostaglandin $F_2$-like compounds are produced in vivo in humans by a non-cyclooxygenase, free radical-catalyzed mechanism. Proc Natl Acad Sci USA 1990; 87(23):9383-9387.PM:2123555
21. Bertola A, Mathews S, Ki S H, Wang H, Gao B. Mouse model of chronic and binge ethanol feeding (the NIAAA model). Nat Protoc 2013; 8(3):627-637.PM:23449255
22. Fessel J P, Hulette C, Powell S, Roberts Li, Zhang J. Isofurans, but not $F_2$-isoprostanes, are increased in the substantia nigra of patients with Parkinson's disease and with dementia with Lewy body disease. J Neurochem 2003; 85(3):645-650.PM:12694390
23. Binder C J. Naturally occurring IgM antibodies to oxidation-specific epitopes. Adv Exp Med Biol 2012; 750:2-13.PM:22903662
24. Chou M Y, Hartvigsen K, Hansen L F et al. Oxidation-specific epitopes are important targets of innate immunity. J Intern Med 2008; 263(5):479-488.PM:18410591
25. Lieber C S. Role of oxidative stress and antioxidant therapy in alcoholic and nonalcoholic liver diseases. Adv Pharmacol 1997; 38:601-628.PM:8895826
26. Wu D, Cederbaum A I. Alcohol, oxidative stress, and free radical damage. Alcohol Res Health 2003; 27(4):277-284.PM:15540798
27. Milne G L, Sanchez S C, Musiek E S, Morrow J D. Quantification of $F_2$-isoprostanes as a biomarker of oxidative stress. Nat Protoc 2007; 2(1):221-226.PM:17401357
28. Ivester P, Roberts II, Young T et al. Ethanol self-administration and alterations in the livers of the cynomolgus monkey, *Macaca fascicularis*. Alcohol Clin Exp Res 2007; 31(1):144-155.PM:17207113
29. Raszeja-Wyszomirska J, Safranow K, Milkiewicz M, Milkiewicz P, Szynkowska A, Stachowska E. Lipidic last breath of life in patients with alcoholic liver disease. Prostaglandins Other Lipid Mediat 2012; 99(1-2):51-56.PM:22706383
30. Konishi M, Iwasa M, Araki J et al. Increased lipid peroxidation in patients with non-alcoholic fatty liver disease and chronic hepatitis C as measured by the plasma level of 8-isoprostane. J Gastroenterol Hepatol 2006; 21(12):1821-1825.PM:17074020
31. Davies S S, Bodine C, Matafonova E et al. Treatment with a gamma-ketoaldehyde scavenger prevents working memory deficits in hApoE4 mice. J Alzheimers Dis 2011; 27(1):49-59.PM:21709376
32. Salomon R G. Isolevuglandins, oxidatively truncated phospholipids, and atherosclerosis. Ann N Y Acad Sci 2005; 1043:327-342.PM:16037255
33. Salomon R G, Subbanagounder G, O'Neil J et al. Levuglandin E2-protein adducts in human plasma and vasculature. Chem Res Toxicol 1997; 10(5):536-545.PM:9168251
34. Smathers R L, Galligan J J, Shearn C T et al. Susceptibility of L-FABP-/- mice to oxidative stress in early-stage alcoholic liver. J Lipid Res 2013; 54(5):1335-1345.PM:23359610
35. Stewart S F, Vidali M, Day C P, Albano E, Jones D E. Oxidative stress as a trigger for cellular immune responses in patients with alcoholic liver disease. Hepatology 2004; 39(1):197-203.PM:14752838
36. Mottaran E, Stewart S F, Rolla R et al. Lipid peroxidation contributes to immune reactions associated with alcoholic liver disease. Free Radic Biol Med 2002; 32(1):38-45.PM:11755315
37. Chedid A, Mendenhall C L, Moritz T E et al. Cell-mediated hepatic injury in alcoholic liver disease. Veterans Affairs Cooperative Study Group 275. Gastroenterology 1993; 105(1):254-266.PM:8514042
38. Lin F, Taylor N J, Su H et al. Alcohol dehydrogenase-specific T-cell responses are associated with alcohol consumption in patients with alcohol-related cirrhosis. Hepatology 2013; 58(1):314-324.PM:23424168
39. Rao R. Endotoxemia and gut barrier dysfunction in alcoholic liver disease. Hepatology 2009; 50(2):638-644.PM:19575462
40. Hritz I, Mandrekar P, Velayudham A et al. The critical role of toll-like receptor (TLR) 4 in alcoholic liver disease is independent of the common TLR adapter MyD88. Hepatology 2008; 48(4):1224-1231.PM:18792393
41. Soares J B, Pimentel-Nunes P, Roncon-Albuquerque R, Leite-Moreira A. The role of lipopolysaccharide/toll-like receptor 4 signaling in chronic liver diseases. Hepatol Int 2010; 4(4):659-672.PM:21286336
42. Wright S D, Ramos R A, Tobias P S, Ulevitch R J, Mathison J C. CD14, a receptor for complexes of lipopolysaccharide (LPS) and LPS binding protein. Science 1990; 249(4975):1431-1433.PM:1698311
43. Markiewski M M, Lambris J D. The role of complement in inflammatory diseases from behind the scenes into the spotlight. Am J Pathol 2007; 171(3):715-727.PM:17640961
44. Li W, Laird J M, Lu L et al. Isolevuglandins covalently modify phosphatidylethanolamines in vivo: detection and quantitative analysis of hydroxylactam adducts. Free Radic Biol Med 2009; 47(11):1539-1552.PM:19751823
45. Bykov I, Jauhiainen M, Olkkonen V M et al. Hepatic gene expression and lipid parameters in complement C3(-/-) mice that do not develop ethanol-induced steatosis. J Hepatol 2007; 46(5):907-914.PM:17321001
46. Bykov I, Junnikkala S, Pekna M, Lindros K O, Meri S. Complement $C_3$ contributes to ethanol-induced liver steatosis in mice. Ann Med 2006; 38(4):280-286.PM:16754259

47. Kalant D, Cain S A, Maslowska M, Sniderman A D, Cianflone K, Monk P N. The chemoattractant receptor-like protein C5L2 binds the C3a des-Arg77/acylation-stimulating protein. J Biol Chem 2003; 278(13):11123-11129.PM:12540846
48. Schieferdecker H L, Schlaf G, Koleva M, Gotze O, Jungermann K. Induction of functional anaphylatoxin $C_5a$ receptors on hepatocytes by in vivo treatment of rats with IL-6. J Immunol 2000; 164(10):5453-5458.PM:10799912
49. Mack C, Jungermann K, Gotze O, Schieferdecker H L. Anaphylatoxin $C_5a$ actions in rat liver: synergistic enhancement by $C_5a$ of lipopolysaccharide-dependent alpha(2)-macroglobulin gene expression in hepatocytes via IL-6 release from Kupffer cells. J Immunol 2001; 167(7):3972-3979.PM:11564816
50. Zagol-Ikapitte I, Amarnath V, Jadhav S, Oates J A, Boutaud O. Determination of 3-methoxysalicylamine levels in mouse plasma and tissue by liquid chromatography-tandem mass spectrometry: application to in vivo pharmacokinetics studies. J Chromatogr B Analyt Technol Biomed Life Sci 2011; 879(15-16):1098-1104.PM:21489890
51. Davies S S, Brantley E J, Voziyan P A et al. Pyridoxamine analogues scavenge lipid-derived gamma-ketoaldehydes and protect against H2O2-mediated cytotoxicity. Biochemistry 2006; 45(51):15756-15767.PM:17176098
52. Carithers R L, Jr., Herlong H F, Diehl A M et al. Methylprednisolone therapy in patients with severe alcoholic hepatitis. A randomized multicenter trial. Ann Intern Med 1989; 110(9):685-690.PM:2648927
53. Lucey M R, Mathurin P, Morgan T R. Alcoholic hepatitis. N Engl J Med 2009; 360(26):2758-2769.PM:19553649
54. Mathurin P, Mendenhall C L, Carithers R L, Jr. et al. Corticosteroids improve short-term survival in patients with severe alcoholic hepatitis (A H): individual data analysis of the last three randomized placebo controlled double blind trials of corticosteroids in severe A H. J Hepatol 2002; 36(4):480-487.PM:11943418
55. Naveau S, Chollet-Martin S, Dharancy S et al. A double-blind randomized controlled trial of infliximab associated with prednisolone in acute alcoholic hepatitis. Hepatology 2004; 39(5):1390-1397.PM:15122768
56. Mathurin P, Abdelnour M, Ramond M J et al. Early change in bilirubin levels is an important prognostic factor in severe alcoholic hepatitis treated with prednisolone. Hepatology 2003; 38(6):1363-1369.PM:14647046
57. Akriviadis E, Botla R, Briggs W, Han S, Reynolds T, Shakil O. Pentoxifylline improves short-term survival in severe acute alcoholic hepatitis: a double-blind, placebo-controlled trial. Gastroenterology 2000; 119(6):1637-1648.PM:11113085
58. De B K, Gangopadhyay S, Dutta D, Baksi S D, Pani A, Ghosh P. Pentoxifylline versus prednisolone for severe alcoholic hepatitis: a randomized controlled trial. World J Gastroenterol 2009; 15(13):1613-1619.PM:19340904
59. Mathurin P, Louvet A, Duhamel A et al. Prednisolone with vs without pentoxifylline and survival of patients with severe alcoholic hepatitis: a randomized clinical trial. JAMA 2013; 310(10):1033-1041.PM:24026598
60. Albano E, Vidali M. Immune mechanisms in alcoholic liver disease. Genes Nutr 2010; 5(2):141-147.PM:19809845
61. Stewart S F, Vidali M, Day C P, Albano E, Jones D E. Oxidative stress as a trigger for cellular immune responses in patients with alcoholic liver disease. Hepatology 2004; 39(1):197-203.PM:14752838
62. Stewart S F, Vidali M, Day C P, Albano E, Jones D E. Oxidative stress as a trigger for cellular immune responses in patients with alcoholic liver disease. Hepatology 2004; 39(1):197-203.PM:14752838
63. Cresci G A, Bush K, Nagy L E. Tributyrin supplementation protects mice from acute ethanol-induced gut injury. Alcohol Clin Exp Res 2014; 38(6):1489-1501.PM:24890666
64. Lieber C S. The discovery of the microsomal ethanol oxidizing system and its physiologic and pathologic role. Drug Metab Rev 2004; 36(3-4):511-529.PM:15554233
65. Perrot N, Nalpas B, Yang C S, Beaune P H. Modulation of cytochrome P450 isozymes in human liver, by ethanol and drug intake. Eur J Clin Invest 1989; 19(6):549-555.PM:2515975
66. Lieberman M A, Marks A D. Ethanol Metabolism. Basic Medical Biochemistry: A Clinical Approach. Wolters Kluwer; 2012.
67. Russell T D, Schaack J, Orlicky D J et al. Adipophilin regulates maturation of cytoplasmic lipid droplets and alveolae in differentiating mammary glands. J Cell Sci 2011; 124(Pt 19):3247-3253.PM:21878492
68. Zagol-Ikapitte I A, Matafonova E, Amarnath V et al. Determination of the Pharmacokinetics and Oral Bioavailability of Salicylamine, a Potent gamma-Ketoaldehyde Scavenger, by L C/M S/M S. Pharmaceutics 2010; 2(1):18-29.PM:21822464
69. Reagan-Shaw S, Nihal M, Ahmad N. Dose translation from animal to human studies revisited. FASEB J 2008; 22(3):659-661.PM:17942826
70. Guidance for Industry: Estimating the Maximum Safe Starting Dose in Initial Clinical Trials for Therapeutics in Adult Healthy Volunteers. Center for Drug Evaluation and Research. Rockville, M D, USA: U.S. Food and Drug Administration; 2005.

The invention claimed is:
1. A method for inhibiting inflammasome activation in an animal with or at risk of nonalcoholic fatty liver disease (NAFLD), alcoholic liver disease (ALD) or nonalcoholic steatohepatitis (NASH), thereby inhibiting or treating the nonalcoholic fatty liver disease (NAFLD), alcoholic liver disease (ALD) or nonalcoholic steatohepatitis (NASH), comprising the step of administering to the animal an effective amount of a compound selected from salicylamine, ethylsalicylamine, and methylsalicylamine, or a pharmaceutically acceptable salt thereof.
2. The method of claim 1, wherein the compound is salicylamine.
3. A method for reducing serum isoprostane levels in an animal with nonalcoholic fatty liver disease (NAFLD), alcoholic liver disease (ALD) or nonalcoholic steatohepatitis (NASH), thereby inhibiting or treating the nonalcoholic fatty liver disease (NAFLD), alcoholic liver disease (ALD) or nonalcoholic steatohepatitis (NASH), comprising the step of administering to the animal an effective amount of a compound selected from salicylamine, ethylsalicylamine, and methylsalicylamine, or a pharmaceutically acceptable salt thereof.
4. The method of claim 3, wherein the compound is salicylamine.
5. The method of claim 1, wherein the inflammasome is an NLRP inflammasome.
6. The method of claim 1, wherein the inflammasome is NLRP3.

* * * * *